(12) United States Patent
Kraft et al.

(10) Patent No.: US 7,854,753 B2
(45) Date of Patent: Dec. 21, 2010

(54) PHOTOKINETIC DELIVERY OF BIOLOGICALLY ACTIVE SUBSTANCES USING PULSED INCOHERENT LIGHT

(75) Inventors: Edward R. Kraft, New York, NY (US); Gabriela Kulp, Mohrsville, PA (US)

(73) Assignee: Photokinetix, Inc., New York, NY (US)

(*) Notice: Subject to any disclaimer, the term of this patent is extended or adjusted under 35 U.S.C. 154(b) by 239 days.

(21) Appl. No.: 12/215,899

(22) Filed: Jun. 30, 2008

(65) Prior Publication Data

US 2009/0156463 A1    Jun. 18, 2009

Related U.S. Application Data

(63) Continuation of application No. 10/679,112, filed on Oct. 3, 2003, now Pat. No. 7,458,982.

(60) Provisional application No. 60/479,501, filed on Jun. 17, 2003, provisional application No. 60/416,361, filed on Oct. 4, 2002.

(51) Int. Cl.
*A61N 5/00* (2006.01)
*A61K 38/00* (2006.01)

(52) U.S. Cl. .................. 607/88; 604/20; 514/2

(58) Field of Classification Search .................. None
See application file for complete search history.

(56) References Cited

U.S. PATENT DOCUMENTS

| | | |
|---|---|---|
| 4,702,732 A | 10/1987 | Powers et al. |
| 4,786,277 A | 11/1988 | Powers et al. |
| 4,886,489 A | 12/1989 | Jacobsen et al. |
| 4,931,046 A | 6/1990 | Newman |
| 4,940,456 A | 7/1990 | Sibalis et al. |
| 5,016,615 A | 5/1991 | Driller et al. |
| 5,047,007 A | 9/1991 | McNichols et al. |
| 5,084,008 A | 1/1992 | Phipps |
| 5,115,805 A | 5/1992 | Bommannan et al. |
| 5,135,480 A | 8/1992 | Bannon et al. |
| 5,156,846 A | 10/1992 | Petersen et al. |
| 5,167,616 A | 12/1992 | Haak et al. |
| 5,203,768 A | 4/1993 | Haak et al. |
| 5,221,254 A | 6/1993 | Phipps |
| 5,224,927 A | 7/1993 | Tapper |
| 5,231,975 A | 8/1993 | Bommannan et al. |
| 5,258,453 A | 11/1993 | Kopecek et al. |
| 5,306,235 A | 4/1994 | Haynes |
| 5,306,485 A | 4/1994 | Robinson et al. |
| 5,322,502 A | 6/1994 | Theeuwes et al. |
| 5,323,769 A | 6/1994 | Bommannan et al. |
| 5,362,308 A | 11/1994 | Chien et al. |
| 5,403,275 A | 4/1995 | Phipps |
| 5,421,816 A | 6/1995 | Lipkovker |
| 5,423,739 A | 6/1995 | Phipps et al. |
| 5,426,387 A | 6/1995 | Teillaud et al. |
| 5,464,387 A | 11/1995 | Haak et al. |
| 5,527,350 A | 6/1996 | Grove et al. |
| 5,527,797 A | 6/1996 | Eisenberg et al. |
| 5,533,971 A | 7/1996 | Phipps |
| 5,540,654 A | 7/1996 | Riviere et al. |
| 5,573,503 A | 11/1996 | Untereker et al. |
| 5,591,124 A | 1/1997 | Phipps |
| 5,617,851 A | 4/1997 | Lipkovker |
| 5,636,632 A | 6/1997 | Bommannan et al. |
| 5,637,084 A | 6/1997 | Kontturi et al. |
| 5,667,487 A | 9/1997 | Henley |
| 5,668,120 A | 9/1997 | Shinoda et al. |
| 5,668,170 A | 9/1997 | Gyory |
| 5,693,010 A | 12/1997 | Ledger et al. |
| 5,698,207 A | 12/1997 | Staats |
| 5,700,481 A | 12/1997 | Iga et al. |
| 5,736,580 A | 4/1998 | Huntington et al. |
| 5,749,847 A | 5/1998 | Zewert et al. |
| 5,771,890 A | 6/1998 | Tamada |
| 5,811,465 A | 9/1998 | Huntington et al. |
| 5,814,599 A | 9/1998 | Mitragotri et al. |
| 5,817,144 A | 10/1998 | Gregory |
| 5,843,014 A | 12/1998 | Lattin et al. |
| 5,861,439 A | 1/1999 | Gyory et al. |
| 5,908,400 A | 6/1999 | Higo et al. |

(Continued)

FOREIGN PATENT DOCUMENTS

DE    10208678    9/2002

(Continued)

OTHER PUBLICATIONS

Banga, A.K. Dr., "Drug Delivery Today", Business Briefing: Pharmatech, 2002, pp. 150-153.

Datye, A.K. et al., "TiO₂ Photocatalysts For The Treatment Of Hazardous Waste: The Intrinsic Dependence on Particle Size And Mechanisms Of Catalyst Deactivation", Technical Completion Report, Project Number, WERC 92-94, Aug. 1994, Waste-management Education and Research Consortium Technical Development Annual Report, 1993-1994, vol. 1, pp. 403-425, Las Cruces, New Mexico: Waste-management Education and Research Consortium, 1994.

Dijkstra et al., "Photodynamic therapy with violet light and topical delta-aminolaevulinic acid in the treatment of actinic keratosis, Bowen's disease and basal cell carcinoma", Journal of the European Academy of Dermatology and Venereology, vol. 15, pp. 550-554 (2001).

(Continued)

*Primary Examiner*—Anand U Desai
(74) *Attorney, Agent, or Firm*—Ropes & Gray LLP

(57) ABSTRACT

The invention relates generally to transdermal and transmembrane delivery of biologically active substances through the skin, sub-dermal tissues, blood vessels and cellular membranes without causing damage to the cellular surface, tissue or membrane. The invention provides compositions and methods for enhanced transdermal and transmembrane delivery of biologically active substances using pulsed incoherent light. The invention further provides a device for the application of the pulsed incoherent light to cellular surfaces and membranes using those compositions and methods.

28 Claims, 18 Drawing Sheets

U.S. PATENT DOCUMENTS

| | | |
|---|---|---|
| 5,941,821 A | 8/1999 | Chou |
| 5,947,921 A | 9/1999 | Johnson et al. |
| 5,954,675 A | 9/1999 | Dellagatta |
| 5,961,482 A | 10/1999 | Chien et al. |
| 5,968,006 A | 10/1999 | Hofmann |
| 5,999,678 A | 12/1999 | Murphy-Chutorian et al. |
| 6,002,961 A | 12/1999 | Mitragotri et al. |
| 6,004,309 A | 12/1999 | Phipps |
| 6,009,345 A | 12/1999 | Hofmann |
| 6,018,678 A | 1/2000 | Mitragotri et al. |
| 6,023,629 A | 2/2000 | Tamada |
| 6,024,717 A | 2/2000 | Ball et al. |
| 6,024,968 A | 2/2000 | Suess et al. |
| 6,030,374 A | 2/2000 | McDaniel |
| 6,041,253 A | 3/2000 | Kost et al. |
| 6,048,545 A | 4/2000 | Keller et al. |
| 6,057,374 A | 5/2000 | Huntington et al. |
| 6,059,736 A | 5/2000 | Tapper |
| 6,071,944 A | 6/2000 | Rodgers et al. |
| 6,083,190 A | 7/2000 | Gyory et al. |
| 6,085,115 A | 7/2000 | Weaver et al. |
| 6,106,514 A | 8/2000 | O'Donnell, Jr. |
| 6,139,537 A | 10/2000 | Tapper |
| 6,142,939 A | 11/2000 | Eppstein et al. |
| 6,148,231 A | 11/2000 | Henley |
| 6,162,211 A | 12/2000 | Tankovich et al. |
| 6,167,301 A | 12/2000 | Flower et al. |
| 6,167,302 A | 12/2000 | Millot |
| 6,168,587 B1 | 1/2001 | Bellhouse et al. |
| 6,190,315 B1 | 2/2001 | Kost et al. |
| 6,216,033 B1 | 4/2001 | Southam et al. |
| 6,221,068 B1 | 4/2001 | Fried et al. |
| 6,234,990 B1 | 5/2001 | Rowe et al. |
| 6,235,013 B1 | 5/2001 | Tapper |
| 6,238,381 B1 | 5/2001 | Tapper |
| 6,251,099 B1 | 6/2001 | Kollias et al. |
| 6,283,956 B1 | 9/2001 | McDaniel |
| 6,289,241 B1 | 9/2001 | Phipps |
| 6,295,469 B1 | 9/2001 | Linkwitz et al. |
| 6,322,532 B1 | 11/2001 | D'Sa et al. |
| 6,324,424 B1 | 11/2001 | Ledger et al. |
| 6,379,324 B1 | 4/2002 | Gartstein et al. |
| 6,385,487 B1 | 5/2002 | Henley |
| 6,387,059 B1 | 5/2002 | Marchitto et al. |
| 6,387,089 B1 | 5/2002 | Kreindel et al. |
| 6,389,313 B1 | 5/2002 | Marchitto et al. |
| 6,391,643 B1 | 5/2002 | Chen et al. |
| 6,398,753 B2 | 6/2002 | McDaniel |
| 6,402,732 B1 | 6/2002 | Flower et al. |
| RE37,796 E | 7/2002 | Henley |
| 6,421,561 B1 | 7/2002 | Morris |
| 6,425,892 B2 | 7/2002 | Southam et al. |
| 6,447,503 B1 | 9/2002 | Wynne et al. |
| 6,491,657 B2 | 12/2002 | Rowe et al. |
| 7,150,710 B2 | 12/2006 | Haber et al. |
| 2002/0026225 A1 | 2/2002 | Segal |
| 2002/0127198 A1 | 9/2002 | Rothbard et al. |
| 2002/0197262 A1 | 12/2002 | Hasan et al. |
| 2003/0045916 A1 | 3/2003 | Anderson et al. |
| 2003/0099264 A1 | 5/2003 | Dantus et al. |
| 2003/0130709 A1 | 7/2003 | Haber et al. |
| 2003/0171795 A1 | 9/2003 | Walmsley et al. |
| 2003/0191458 A1 | 10/2003 | Diamond et al. |
| 2003/0219056 A1 | 11/2003 | Yager et al. |
| 2004/0048842 A1 | 3/2004 | McMillan |
| 2004/0073277 A1 | 4/2004 | Geronemus et al. |
| 2004/0122492 A1 | 6/2004 | Harth et al. |
| 2004/0167501 A1 | 8/2004 | Island et al. |
| 2004/0225339 A1 | 11/2004 | Yaroslavsky et al. |
| 2005/0010271 A1 | 1/2005 | Merchant |
| 2005/0045189 A1 | 3/2005 | Jay |
| 2005/0070976 A1 | 3/2005 | Samuel et al. |
| 2005/0113288 A1 | 5/2005 | Utecht et al. |
| 2005/0148567 A1 | 7/2005 | Kjellbotn et al. |
| 2005/0203593 A1 | 9/2005 | Shanks et al. |
| 2005/0222555 A1 | 10/2005 | Manstein et al. |
| 2005/0245998 A1 | 11/2005 | Pruitt et al. |
| 2006/0104859 A1 | 5/2006 | Tribelsky |
| 2006/0173514 A1 | 8/2006 | Biel et al. |
| 2006/0265028 A1 | 11/2006 | Houle et al. |
| 2006/0271024 A1 | 11/2006 | Gertner et al. |
| 2007/0129778 A1 | 6/2007 | Dougal |
| 2007/0185552 A1 | 8/2007 | Masotti et al. |
| 2007/0219600 A1 | 9/2007 | Gertner et al. |
| 2008/0234669 A1 | 9/2008 | Kauvar |
| 2008/0255498 A1 | 10/2008 | Houle |
| 2009/0012515 A1 | 1/2009 | Hoenig et al. |
| 2009/0048557 A1 | 2/2009 | Yeshurun et al. |

FOREIGN PATENT DOCUMENTS

| | | |
|---|---|---|
| EP | 1 238 651 | 9/2002 |
| EP | 1 340 520 | 9/2003 |
| JP | 2000237230 | 9/2000 |
| WO | WO-92/10995 | 7/1992 |
| WO | WO-94/15666 | 7/1994 |
| WO | WO-98/02138 | 1/1998 |
| WO | WO-98/19652 | 5/1998 |
| WO | WO-99/30705 | 6/1999 |
| WO | WO-01/74811 | 10/2001 |
| WO | WO-02/22120 | 3/2002 |
| WO | WO-02/083088 | 10/2002 |
| WO | WO-02/100326 | 12/2002 |

OTHER PUBLICATIONS

Huang et al., "The Study of the Photokinetic effect and Mechanism of Ultrafine Ti02 Particles on U937 Cells", J. of Photochemistry and Photobiology-A Chemistry, vol. 108, 1997, pp. 229-233.

Jiang, F. N, et al., "Enhanced Photodynamic Killing of Target Cells by Either Monoclonal Antibody or Low Density Lipoprotein Mediated Delivery Systems", Journal of Controlled Release, Elsevier Science Publishers B.V. Amsterdam, NL, vol. 19, No. 1/3. 1992.

King, T., "A Review of Needlefree Injection Technologies", World Pharma Web (Pharma Venturas, Ltd.), article 4, 2002: 1-5.

Kost, J., "Ultrasound and Transdermal Transport for Drug Delivery and Diagnostics", Pharmaceutical Technology (PharmaTech) 2001: pp. 196-202.

McNeil, L.E. et al., "Orientation Dependence in Near-Field Scattering from TiO2 Particles", Applied Optics, vol. 40, No. 22, Aug. 1, 2001, 3726-3736.

Panchagnula, R., "Transdermal Delivery of Drugs", Indian Journal of Pharmacology, 29, 1997, pp. 140-156.

PHOTOKINETIC DELIVERY OF BIOLOGICALLY ACTIVE SUBSTANCES USING PULSED INCOHERENT LIGHT

CROSS REFERENCE TO RELATED APPLICATIONS

This application is a continuation application of U.S. Ser. No. 10/679,112, filed on Oct. 3, 2003, which claims the benefit of the filing dates under 35 U.S.C. §119(e) to U.S. Provisional Patent Applications 60/416,361 and 60/479,501, filed on Oct. 4, 2002 and Jun. 17, 2003, respectively, the contents of each of the above-referenced applications are incorporated herein by reference.

The Sequence Listing associated with this application is being submitted electronically via EFS-Web in text format, and is hereby incorporated by reference into the specification. The name of the text file containing the Sequence Listing is 002162_0001_102_Sequence_Listing.txt. The text file is 1,421 bytes in size, and was created on Aug. 6, 2010.

TECHNICAL FIELD OF THE INVENTION

This invention relates to photokinetic delivery of biologically active substances from an outer mammalian skin surface to an underlying tissue or blood vessel (transdermal) and from an extracellular environment to intracellular environment (transmembrane). More particularly, the invention provides compositions for enhanced transdermal and transmembrane delivery of biologically active substances using pulsed incoherent light. In addition, the invention provides methods and devices for application of pulsed incoherent light to an area of mammalian skin or membrane for safe and efficient transdermal and transmembrane delivery of biologically active substances through the skin surface or cellular membrane.

BACKGROUND OF THE INVENTION

Therapeutic agents or biologically active substances can be administered to vital tissues and organs in a mammal by a plethora of delivery routes including, for example, oral, nasal, aural, anal, dermal, ocular, pulmonary, intravenous, intramuscular, intraarterial, intraperitoneal, mucosal, sublingual, subcutaneous, and intracranial routes. In the last decade, transdermal delivery of biologically active substances has gained momentum due to the advantages it provides over those of conventional dosage routes, such as oral and intravenous administration. For example, biologically active substances or drugs delivered transdermally avoids deactivation caused by pH and digestive enzymes upon passage of the active substance through the gastrointestinal (GI) tract. In addition, other advantages of transdermal delivery include, but are not limited to, single application regimens or decreased dosages, increased patient compliance, high percentage of drug reaching the systemic circulation, sustained activity for drugs having short half-lives, controlled release of drugs (no "burst effect"), ability to quickly terminate drug dosing causing adverse effects and administration of drugs without hypodermic injection.

The success of transdermal delivery in a mammal relies on the ability of biologically active substances to penetrate the outer layer of the epidermis known as the stratum corneum. The stratum corneum is comprised mainly of about 10 to about 20 layers of flattened dead cells (corneocytes) filled with keratin. Lipids, such as free fatty acids, cholesterol, and ceramides, connect the regions between the keratinized cells, forming a brick and mortar-like structure. In mammals, this structure primarily serves as a barrier to chemicals and biological agents, including bacteria, fungus, and viruses.

The penetration of biologically active substances through the stratum corneum occurs by either passive or active transport mechanisms. Passive delivery or diffusion relies on a concentration density gradient between the drug at the outer surface and the inner surface of the skin. The diffusion rate is proportional to the gradient and is modulated by a molecule's size, hydrophobicity, hydrophilicity and other physiochemical properties as well as the area of the absorptive surface. Examples of passive delivery systems include transdermal patches for controlled delivery of, for example, nitroglycerine (angina), scopolamine (motion sickness), fentanyl (pain control), nicotine (smoking cessation), estrogen (hormone replacement therapy), testosterone (male hypogonadism), clonidine (hypertension), and lidocaine (topical anesthesia). The controlled delivery of these drugs can include the use of polymer matrices, reservoirs containing drugs with rate-controlling membranes and drug-in-adhesive systems.

In contrast, active delivery relies on ionization of the drug or other pharmacologically active substances and on means for propelling the charged ions through the skin. The rate of active transport varies with the method used to increase movement and propulsion of ions, but typically this transport provides a faster delivery of biologically active substances than that of passive diffusion. Active transport delivery systems include methods such as iontophoresis, sonophoresis, and thermal microporation.

Iontophoresis is a technique used to guide one or more therapeutic ions in solution into the tissues and blood vessels of the body by means of a galvanic or direct electrical current supplied to wires that are connected to skin-interfacing electrodes. Although ionotophoresis provides a method for controlled drug delivery, irreversible skin damage can occur from galvanic and pH burns resulting from electrochemical reactions that occur at the electrode and skin interface. This reaction precludes the use of this method when extended application times are needed to achieve prolonged systemic effects.

Sonophoresis is another active transport method that uses ultrasound varying in frequency from 20 kHz to 16 MHz to transport substances across the stratum corneum. Sonophoresis affects biological tissues by three main routes—thermal, cavitational and acoustic streaming. For example, ultrasound will increase the temperature of a given medium, and the absorption coefficient of that medium increases proportionally with ultrasound frequency. Cavitation can occur when ultrasound-induced pressure variation causes rapid growth and collapse of gas bubbles, causing structural alteration of the skin. Acoustic streaming, a phenomenon that affects surrounding tissue structure, can occur when shear stresses result from ultrasound reflections, distortions, and oscillations of cavitation bubbles. It has also been postulated that ultrasound interacts with the ordered lipids comprising the stratum corneum, forming an opening for drug passage. The interruption of the connective layer by any of the above-identified routes can lead to an area of skin that is predisposed to sloughing as well as bacterial and viral infiltration.

Microporation is an active transport method used to produce micropores in the stratum corneum. Microporation is accomplished by various means, including ablating the stratum corneum by local rapid heating of water, puncturing the stratum corneum with a micro-lancet calibrated to form a specific pore diameter, ablating the stratum corneum by focusing a tightly focused beam of sonic energy, hydraulically puncturing the stratum corneum with a high pressure fluid jet, and puncturing the stratum corneum with short pulses of electricity. Laser energy can also be used to cause microporation. Although the diameter of the hole can be controlled, microporation can cause irritation, damage and/or removal of stratum corneum cells.

Because of the inherent problems of the above-identified methods, a need exists for a safe and efficient transdermal drug delivery that eliminates side-effects and damage to the barrier function or appearance of the skin caused by drug administration. It would therefore be desirable to provide compositions, methods, and apparatuses to address these problems.

SUMMARY OF THE INVENTION

The problems associated with active transdermal drug delivery can be overcome by this invention, which relates to novel compositions, methods, and devices for photokinetic transdermal and transmembrane delivery of biologically active substances through the stratum corneum or a biological membrane without causing damage to this layer or underlying tissues and without denaturation and/or degradation of the biologically active substance being administered.

The compositions, methods, and devices described herein preferably use pulsed incoherent light to focus and deliver biologically active substances through the outer surface of the skin to an underlying tissue or blood vessel or from an extracellular environment to an intracellular environment. In some embodiments, compositions containing only biologically active substances are used as delivery media, whereas in other embodiments, biologically active substances used in combination with other components are used as delivery media.

Methods and devices employing pulsed incoherent light are used to actively transport a biologically active medium through the outer surface of the skin or cell membrane. This provides many advantages, including the ability to create a pathway for drug delivery without causing damage to the skin or membrane while being able to excite biologically active molecules without degrading or denaturing them. In addition, the rate of delivery of the biologically active component can be controlled and sustained by modulating the wavelength, pulse rate, duty cycle and intensity of the light being used to photokinetically propagate the component through the skin or membrane. Finally, the use of a light pad containing more than one light source permits light to expose a biologically active medium over a well-defined surface area. The skin permeability can be enhanced through the use of compositions, methods and devices described herein.

DETAILED DESCRIPTION OF THE INVENTION

Figure 1:
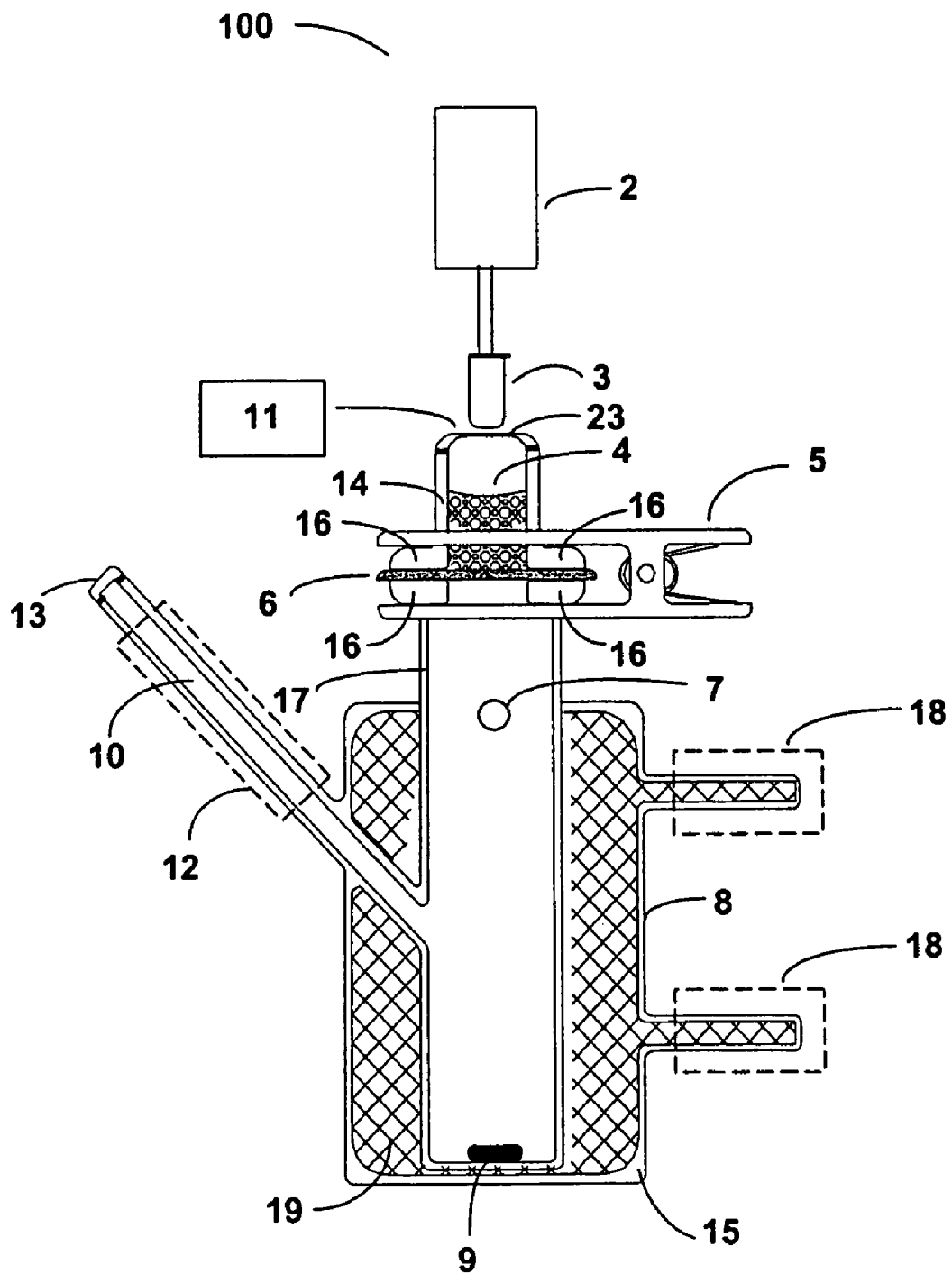
FIG. 1 shows a Franz skin diffusion device equipped with a light source to generate pulses of defined wavelengths for testing of biologically active substances.

Unless otherwise defined herein, scientific and technical terms used in connection with the invention shall have the meanings that are commonly understood by those of ordinary skill in the art. Further, unless otherwise required by context, singular terms shall include pluralities and plural terms shall include the singular. Generally, nomenclatures used in connection with, and techniques of, column chromatography, optics, chemistry, peptide and protein chemistries, nucleic acid chemistry and molecular biology described herein are those well known and commonly used in the art.

The following terms, unless otherwise indicated, shall be understood to have the following meanings:

The term "biologically active substance" refers generally to any chemical, drug, antibiotic, peptide, hormone, protein, DNA, RNA and mixtures thereof that affects biological pathways or interacts with cellular components.

The term "chemical" denotes any naturally found or synthetically made small molecule or polymer. A chemical can be a polar (hydrophilic), non-polar (hydrophobic), oleophobic or oleophilic compound. Although not an exhaustive list, examples of polar compounds include theophylline-7-acetic acid, sodium ascorbyl phosphate, ascorbic acid, ascorbyl palmitate, pyridoxine, nicotinic acid and lidocaine. Examples of non-polar compounds include theobromine, theophylline, caffeine and nicotinamide. Oleophobic compounds are those compounds lacking affinity for oils and oleophilic compounds are any compounds that have a stronger affinity for oils over that of water. Accordingly, the invention described herein is particularly useful for transport of compounds with chromophores, which can be polar, non-polar, oleophobic, including fluorochemicals, and oleophilic.

The term "drug" denotes any natural or synthetic compound used for therapeutic treatment in mammals. Examples of drugs include, but are not limited to, analgesics, antacids, antianxiety drugs, antiarrhythmics, antibacterials, antibiotics, anticoagulants and thrombolytics, anticonvulsants, antidepressants, antidiarrheals, antiemetics, antifungals, antihistamines, antihypertensives, anti-inflammatories, antieoplastics, antipsychotics, antipyretics, antivirals, barbiturates, beta-blockers, bronchodilators, cold cures, corticosteroids, cough suppressants, cytotoxics, decongestants, diuretics, expectorant, hormones, hypoglycemics, immunosuppressives, laxatives, muscle relaxants, sedatives, sex hormones, sleeping drugs, tranquilizer and vitamins.

Vitamins are organic chemicals that are essential for nutrition in mammals and are typically classified as fat-soluble or water-soluble. Vitamins required to maintain health in humans include, but are not limited to, vitamin A (retinol), precursor to vitamin A (carotene), vitamin $B_1$ (thiamin), vitamin $B_2$ (riboflavin), vitamin $B_3$ (nicotinic acid), vitamin B (pantothenic acid), vitamin C (ascorbic acid), vitamin D (calciferol), vitamin E (tocopherol), vitamin H (biotin) and vitamin K (napthoquinone derivatives).

The term "antibiotic" refers to any natural or synthetic substance that inhibits the growth of or destroys microorganisms in the treatment of infectious diseases. Although not an exhaustive list, examples of antibiotics include amoxicillin, ampicillin, penicillin, clavulanic acid, aztreonam, imipenem, streptomycin, gentamicin, vancomycin, clindamycin, ephalothin, erythromycin, polymyxin, bacitracin, amphotericin, nystatin, rifampicin, teracycline, coxycycline, chloramphenicol and zithromycin.

The term "peptide" refers to a compound that contains 2 to 50 amino acids and/or imino acids connected to one another. The amino acids can be selected from the 20 naturally occurring amino acids. The twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. The amino acids can also be selected from non-natural amino acids such as those found on the following website: http://www.sigmaaldrich.com/img/assets/6040/chemFiles_v1n5_unnaturalaa_small.pdf). Although not an exhaustive list, examples of peptides include glycine-tyrosine, valine-tyrosine-valine, tyrosine-glycine-glycine-phenylalanine-methionine (SEQ ID NO: 1), tyrosine-glycine-glycine-phenylalanine-leucine (SEQ ID NO: 2) and aspartic acid-arginine-valine-tyrosine-isoleucine-histidine-proline-phenylalanine (SEQ ID NO: 3).

The term "hormone" refers to a substance that originates in an organ, gland, or part, which is conveyed through the blood to another part of the body, stimulating it by chemical action to increased functional activity or to increase secretion of another hormone. Although not an exhaustive list, examples of hormones include methionine enkephalin acetate, leucine enkephalin, angiotensin II acetate, β-estradiol, methyl testosterone, progesterone and insulin.

A polypeptide is defined as a chain of greater than 50 amino acids and/or imino acids connected to one another.

A protein is a large macromolecule composed of one or more polypeptide chains. The term "isolated protein" is a protein that by virtue of its origin or source of derivation (1) is not associated with naturally associated components that accompany it in its native state, (2) is free of other proteins from the same species (3) is expressed by a cell from a different species, or (4) does not occur in nature. Thus, a protein that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The terms DNA and RNA as referred to herein mean deoxyribonucleic acid and ribonucleic acid, respectively. The term "polynucleotide" means a polymeric form of nucleotides of at least 10 bases in length, either ribonucleotides or deoxynucleotides or a modified form of either type of nucleotide. The term includes single and double stranded forms.

Gelling agents according to this invention are compounds that can behave as reversible or non-reversible networks. Under certain conditions, a gelling agent can be placed in a solvent to form a viscous solution. Under other conditions, that same gelling agent can be placed in the same or different solvent to form a gel. The role of gelling agents according to the invention is to prevent evaporation loss of the biologically active substance in the appropriate solvent. Examples of gelling agents include, but are not limited to, hydroxyethyl cellulose, Natrasol®, pectines, agar, alginic acid and its salts, guar gum, pectin, polyvinyl alcohol, polyethylene oxide, cellulose and its derivatives, propylene carbonate, polyethylene glycol, hexylene glycol sodium carboxymethylcellulose, polyacrylates, polyoxyethylene-polyoxypropylene block copolymers, pluronics, wood wax alcohols and tyloxapol.

The term "photocatalytic agent" refers to any semiconductor having a wide band gap energy. In an embodiment of the invention, the band gap energy is on the order of about 2.9-3.2 eV. A band gap on this order allows infrared and the entire visible spectrum to be transmitted upon excitation of an electron from the valence band to the conduction band. Without being bound by theory, pulsed incoherent light energy that is stored and released from the wide band gap semiconductor can enhance the bond vibration of a biologically active molecule also present during this excitation. The stimulation of active molecules with the transfer of energy from the semiconductor at discrete wavelengths and pulse rates can enhance the transport of that molecule across biological membranes, while the semiconductor can also protect the skin from harmful ultraviolet (UV) rays by absorbing UV light. By modulating the wavelength of excitation with that of the band gap energy, the production of free radicals is avoided entirely. Accordingly, the use of rutile form of titanium dioxide ($TiO_2$) as the photocatalytic agent is preferred because it has a band gap energy of about 2.9 to 3.0 eV. Other photocatalytic agents suitable for this invention include, but are not limited to, anatase $TiO_2$, brookite $TiO_2$, ZnO, $ZrO_2$ and $Sc_2O_3$. According to the invention, doped semiconductors can also be used.

The term "solvent" according to the invention is any aqueous or organic solvent that can be combined with the biologically active agent to form a solution. In one embodiment, the aqueous solvent is water. In another embodiment, the solvent can be an aqueous solution of either ethyl lactate or propylene glycol, both of which act as permeation enhancers. Alternately, the term "solvent" can also mean an adhesive used to embed a biologically active substance, for example, in a patch. Solvent can also refer to a pharmaceutically-acceptable medium combined with the biologically active substance to be used in powder form.

In another embodiment, the biologically active substance can be emulsified. For example, lipophilic compounds, such as vitamins A, D, and E, can be dispersed in an aqueous solvent to which an emulsifying agent, such as Carbopol or triethanol amine, can be added.

Likewise, in the absence or presence of a solvent, the biologically active agent according to the invention can also be combined with a carrier or adjuvant, a substance that, when added to a therapeutic, speeds or improves its action (The On-Line Medical Dictionary, http://cancerweb.ncl.ac.uk/omd/index.html). Examples of adjuvants include, for example, Freud's adjuvant, ion exchanges, alumina, aluminum stearate, lecithin, buffer substances, such as phosphates, glycine, sorbic acid, potassium sorbate, partial glyceride mixtures of saturated vegetable fatty acids, waters, salts or electrolytes, such as Protamine sulfate, disodium hydrogen phosphate, sodium chloride, zinc slats, colloidal silica, magnesium, trisilicate, celluslose-based substances and polyethylene glycol. Adjuvants for gel base forms may include, for example, sodium carboxymethylcelluslose, polyacrylates, polyoxyethylene-polyoxypropylene-block copolymers, polyethylene glycol and wood wax alcohols.

Although not required to facilitate transdermal delivery, skin-penetrating agents, for example, propylene glycol, DMSO, oleic acid, azone, cineol, liposomes and nanosomes, can also be present in the compositions according to the invention.

The term "donor solution" or "delivery medium" comprises the biologically active substance itself or any mixture of this substance with a solvent, a gelling agent, a photocatalytic agent, a carrier or adjuvant, a skin-penetrating agent, a membrane-penetrating agent and combinations thereof. The biologically active substance, or alternately "active ingredient" does not have to be dissolved in a solvent but can be suspended or emulsified in a solvent. The donor solution or delivery medium can take the form of an aqueous or an organic liquid, a cream, a paste, a powder or a patch.

Although not an exhaustive list, examples illustrating the term "mammal" include human, ape, monkey, rat, pig, dog, rabbit, cat, cow, horse, mouse, and goat. Skin surfaces or membranes according to the invention refer to those of a human or other mammal.

The term "viscous solution" refers to a solution that has an increased resistance to flow.

The term "cellular surface" refers to an outer layer of the skin or a cell membrane. Human skin is comprised of three layers: the epidermis or stratum corneum, the dermis and the hypodermis. The stratum corneum forms the outermost layer of the epidermis and consists of about 10 to about 20 layers of flattened, closely packed cells without nuclei having a thickness of about 10 to about 20 µm. The stratum corneum serves as a barrier to many substances and is selectively permeable to water and other compounds. On the other hand, the epidermis, having a thickness of about 50 to about 100 µm, comprises rapidly dividing basal cells that flatten as they move into the stratum corneum. Finally, the innermost layer of skin, the dermis, comprises a matrix of various cells including collagen and other fibrous proteins and has a thickness of about 1 to about 3 mm. It is this layer that houses hair follicles, sebaceous glands and sweat glands. The term "transdermal" refers to the penetration and movement of a biologically active substance through the epidermis and dermis, or epidermis, dermis and hypodermis.

The term "transmembrane" refers to the penetration and movement of a biologically active substance from an extracellular environment to an intracellular environment.

The term "percutaneous penetration" refers to molecules that have by-passed the dermal blood supply and have diffused into tissue layers below the dermis.

The term "incoherent light" refers to electromagnetic waves that are unorganized and propagate with different phases. The term "pulsed incoherent light" is any incoherent light having a discrete ON and OFF period.

In contrast, "coherent light" refers to all light rays that are in phase and oriented in the exact same direction to produce a concentrated beam of light. Lasers generate these types of rays and can penetrate through materials such as solid media, including metals (e.g., sheet metal).

The term "light emitting diode (LED)" is a device that generally emits incoherent light when an electric voltage is applied across it. Most LEDs emit monochromatic light at a single wavelength that is out of phase with each other. According to the invention, most, if not all, types of LEDs can be used. For example, an LED having output range from red (approximately 700 nm) to blue-violet (approximately 350 nm) can be used. Similarly, infrared-emitting diodes (IRED) which emit infrared (IR) energy at 830 nm or longer can also be used.

"Optically clear medium" or "light pad" is a material that acts as a filter to all wavelengths except those wavelengths emitted from a light source. In a preferred embodiment, the light pad is comprised of clear poly(methyl methacrylate) or clear silicon rubber.

The term "reflective coating or layer" is a material that is coated on at least one surface of the light pad. Those skilled in the art will appreciate that the reflective layer can be a wavelength specific reflective coating (e.g., aluminum, ZnO, silver or any reflective paint).

The term "photokinetic" refers to a change in the rate of motion in response to light, as an increase or decrease in motility with a change in illumination.

One embodiment of the invention relates to compositions for photokinetic transdermal and transmembrane delivery of a biologically active substance using preferably pulsed incoherent light or, alternatively, regulated coherent light. The composition may comprise a biologically active substance as the delivery medium.

The composition may alternatively comprise a biologically active substance and a solvent. The percent of biologically active substance in solvent can be in the range of between 0.0001 to 99.9999% (w/v). Preferably, the biologically active substance is present in a concentration range of between about 0.01% to about 2% (w/v). More preferably, the biologically active substance is present in a concentration range of between about 0.1 mg/ml to about 10 mg/ml in the solvent or, alternatively, between about 0.01% to about 1% (w/v). Due to the high level of permeation achieved by the methods and devices described herein, low concentrations of a biologically active substance in solvent or in other compositions described herein can be used for efficient transdermal or transmembrane delivery.

The composition may instead comprise a biologically active substance, a gelling agent and a solvent. The percent gelling agent in a solution of biologically active substance can vary depending on the type of gelling agent used. For example, Klucel is typically used at 1% (w/v), Natrasol at 1.5% (w/v), Carbopol at 0.75% (w/v), and TEA at 0.25% (w/v).

Still further, the composition may comprise a biologically active substance, a photocatalytic agent and a solvent. Preferably, the photocatalytic agent has a band gap energy of between about 2.9 eV and about 3.2 eV and preferably is present in the composition at a concentration of between about 0.001% and 20% (w/w). More preferably, the photocatalytic agent is present in the composition at a concentration of 2% (w/w).

Finally, compositions according to the invention may comprise a biologically active substance, a gelling agent, a photocatalytic agent and a solvent. Preferably, the photocatalytic agent has a band gap energy of between about 2.9 eV and about 3.2 eV and preferably is present in the composition at a concentration of between about 0.001% and 20% (w/w). More preferably, the photocatalytic agent is present in the composition at a concentration of 2% (w/w). The biologically active substance preferably is present in the composition at a concentration of between about 0.01% and about 2% (w/v). The gelling agent preferably is present in the composition at a concentration of between 0.1% and 10% (w/v).

The biologically active substance of the above compositions may be selected from the group consisting of chemicals, drugs, antibiotics, peptides, hormones, proteins, DNA, RNA and mixtures thereof.

The chemical may be a polar or non-polar compound. The polar compound is preferably selected from the group consisting of theophylline-7 acetic acid, sodium ascorbyl phosphate, ascorbic acid, ascorbyl palmitate, pyridoxine and nicotinic acid. Preferably, the polar compound is pyridoxine. The non-polar compound is preferably selected from the group consisting of theobromine, theophylline, caffeine, and nicotinamide.

The drug may be selected from the group consisting of analgesics, anaesthetics, antacids, antianxiety drugs, antiarrhythmics, antibacterials, antibiotics, anticoagulants and thrombolytics, anticonvulsants, antidepressants, antidiarrheals, antiemetics, antifungals, antihistamines, antihypertensives, anti-inflammatories, antieoplastics, antipsychotics, antipyretics, antivirals, barbiturates, beta-blockers, bronchodilators, cold cures, corticosteroids, cough suppressants, cytotoxics, decongestants, diuretics, expectorants, hormones, hypoglycemics, immunosuppressives, laxatives, muscle relaxants, sedatives, sex hormones, sleeping drugs, tranquilizers, and vitamins. In a preferred embodiment, the anaesthetic is lidocaine.

The compositions according to the invention may also comprise antibiotics as the biologically active substance. Antibiotics according to the invention are selected from the group consisting of amoxicillin, ampicillin, penicillin, clavulanic acid, aztreonam, imipenem, streptomycin, gentamicin, vancomycin, clindamycin, ephalothin, erythromycin, polymyxin, bacitracin, amphotericin, nystatin, rifampicin, teracycline, coxycycline, chloramphenicol, and zithromycin. In a preferred embodiment, the antibiotic is amphotericin B.

Similarly, in another embodiment of the invention, the biologically active substance is a peptide selected from the group consisting of glycine-tyrosine (Gly-Tyr), valine-tyrosine-valine (Val-Tyr-Val), tyrosine-glycine-glycine-phenylalanine-methionine (Tyr-Gly-Gly-Phe-Met) (SEQ ID NO: 1), tyrosine-glycine-glycine-phenylalanine-leucine (Tyr-Gly-Gly-Phe-Leu) (SEQ ID NO: 2), and aspartic acid-arginine-valine-tyrosine-isoleucine-histidine-proline-phenylalanine (Asp-Arg-Val-Tyr-Ile-His-Pro-Phe) (SEQ ID NO: 3).

The hormone may be selected from the group consisting of methionine enkephalin acetate, leucine enkephalin, angiotensin II acetate, β-estradiol, methyl testosterone, progesterone, and insulin.

The protein may be selected from the group consisting of enzymes, non-enzymes, antibodies, and glycoproteins. In one embodiment of the invention, the protein is an enzyme.

Compositions according to the invention can also contain a gelling agent in combination with the biologically active agent and solvent. The gelling agent may be selected from the group consisting of hydroxyethyl cellulose, Natrasol®, pectines, agar, alginic acid and its salts, guar gum, pectin, polyvinyl alcohol, polyethylene oxide, cellulose and its derivatives, propylene carbonate, polyethylene glycol, hexylene glycol sodium carboxymethylcellulose, polyacrylates, polyoxyethylene-polyoxypropylene block copolymers, pluronics, wood wax alcohols, and tyloxapol. In a preferred embodiment, the gelling agent is hydroxypropyl cellulose.

Compositions according to the invention can also include a photocatalytic agent having a wide band gap energy. In one embodiment, the photocatalytic agent has a wide band gap of between about 2.9 eV and about 3.2 eV. In a preferred embodiment, the photocatalytic agent is a rutile form of titanium dioxide ($TiO_2$). In another embodiment, the photocatalytic agent is an anatase form of $TiO_2$, brookite form of $TiO_2$, ZnO, $ZrO_2$ and $Sc_2O_3$.

The composition may also comprise a solvent that is an aqueous or organic solvent. In one embodiment, the aqueous solvent is water. In yet another embodiment, the aqueous solvent is an aqueous solution of ethyl lactate or propylene glycol. Preferably, the water is HPLC grade or purified by means such as reverse osmosis or distillation.

The donor solution or delivery medium according to the invention is comprised of a biologically active substance itself or any mixture of a biologically active substance with a solvent, a gelling agent, a photocatalytic agent, a carrier or adjuvant, a skin-penetrating agent, emulsifier, one or more different biologically active substances, polymers, excipients, coatings and combinations thereof. In essence, the biologically active substance or substances can be combined with any combination of pharmaceutically acceptable components to be delivered to the cellular surface by the method described herein, e.g., photokinetic transdermal and transmembrane delivery. The biologically active substance does not have to be dissolved in a solvent but can be suspended or emulsified in a solvent. The donor solution or delivery medium can take the form of an aqueous or an organic liquid, a cream, a paste, a powder, or a patch. The donor solution can also comprise microspheres or nanospheres of biologically active substances.

The invention described herein is particularly useful for transdermal delivery of compounds containing chromophores. Without being bound by theory, it is believed that the chromophore absorbs photon energy and/or the energy from an excited photocatalytic agent. As the chromophore returns to ground state, it vibrates and generates a very small amount of heat. With each pulse of incoherent light, the chromophore's vibration will incrementally clear a pathway through the skin.

Similarly, the invention described herein is also useful for transmembrane delivery of biologically active substances. For example, a person of skill in the art could inject a therapeutic substance, such as a chemotherapeutic agent, next to a solid tumor mass. An LED that is embedded or held next to the tumor mass can be used to deliver the therapeutic substance from the extracellular environment to the intracellular environment, effectively causing apoptosis in the targeted area.

In addition to compositions, the invention also provides methods of photokinetic delivery of biologically active substances using pulsed incoherent light. One method includes preparing a solution comprising a biologically active substance and a solvent, applying the solution to a cellular surface, illuminating the solution on the cellular surface with a pulsed incoherent light having a selected wavelength, pulse rate and duty cycle and allowing the solution to permeate the cellular surface. In another embodiment, the method includes preparing a solution comprising a biologically active substance, a solvent and a gelling agent, applying the solution to a cellular surface, illuminating the solution on the cellular surface with a pulsed incoherent light having a selected wavelength, pulse rate and duty cycle and allowing the solution to permeate the cellular surface. In yet another embodiment, the method includes preparing a solution comprising a biologically active substance, a solvent, a gelling agent and a photocatalytic agent, applying the solution to a cellular surface, illuminating the solution on the cellular surface with a pulsed incoherent light having a selected wavelength, pulse rate and duty cycle and allowing the solution to permeate the cellular surface. In a preferred embodiment, the cellular surface is an outer layer of a skin of a mammal or a cell membrane.

FIG. 1 illustrates testing device 100 in accordance with the invention. Testing device 100 provides photokinetic transdermal and transmembrane delivery of biologically active substances to a portion of skin or membrane by illuminating the biologically active substance with pulsed incoherent light. Testing device 100 includes a light source 3 that illuminates a biologically active substance in donor cell 4 such that the biologically active substance diffuses into skin 6 with little to no damage to skin 6. Testing device 100 can also be arranged such that the light source 3 illuminating a biologically active substance in donor cell 4 is parallel to a surface on which it is mounted.

Testing device 100 preferably includes a driver circuit 2 that provides control signals to light source 3 such that pulsed incoherent light is provided to donor cell 4. Driver circuit 2 may also provide control signals that control the intensity, direction, and/or frequency of light source 3. A pulsed incoherent light advantageously reduces damage to skin 6 as compared to a continuous light source and provides photokinetic transdermal and transmembrane delivery of biologically active substances within donor cell 4 to skin 6.

Driver circuit 2 may regulate an electrical signal that turns (i.e., switches) light source 3 ON and OFF at a particular frequency. Such an electrical signal may be provided, for example, by a voltage generator. Alternatively, driver circuit 2 may itself be a voltage generator and may produce an electrical signal to control the switching characteristics of light source 3. For example, a voltage generator coupled to light source 3 may provide a square wave to power light source 3. This square wave may have a desired period such that light source 3 provides incoherent light with a desired frequency (e.g., a square wave period of 0.5 seconds would cause light source 3 to switch at 2 Hz).

Light source 3 preferably provides incoherent light (to reduce the damage done to skin 6 during the use of testing device 100). Light source 3 may be, for example, an LED, halogen light source, fluorescent light source, natural light, or other source of light. More particularly, light source 3 can be a light emitting diode (LED) (fluorescence, 350-1700 nm) or an infrared light emitting diode (ILED) or a Mercury-Argon (253-922 nm), pulsed xenon (UV-VIS, 200-1000 nm), deuterium (V, 200-400 nm), deuterium/halogen (UV/VIS/NIR, 200-1700 nm) or tungsten halogen (color/VIS/NIR, 360-1700 nm) light source. Light source 3 preferably is operable in the range from red (approximately 700 nm) to blue-violet (approximately 350 nm). Similarly, infrared-emitting diodes (IREDs) that emit infrared energy at 830 nm or longer may be used.

Light source 3 does not have to be an incoherent light source. Alternatively, light source 3 may be a coherent light source such as, for example, a laser. In that case, driver circuit 2, or other regulation circuitry, is preferably used to turn a coherent light source 3 ON and OFF to reduce the amount of damage to skin 6 while still photokinetically delivering a biologically active substance to donor cell 4. Furthermore, a light regulation/conversion device may be placed between a coherent light source 3 and donor cell 4 to convert the coherent light to incoherent light.

Note that a device such as driver circuit 2 or a controlled voltage generator is not required to pulse light source 3. Alternatively, shutter 11 may be employed between light source 3 and donor cell 4. Such a shutter selectively OPENs and CLOSEs such that donor cell 4 is supplied pulsed incoherent light from light source 3. The speed at which the shutter OPENs and CLOSEs determines the frequency of the light pulsed onto the skin. Filters (not shown) may also be placed between light source 3 and donor cell 4 in order to remove, for example, light of specific wavelengths that may damage skin 6. Alternatively, light source 3 may be immersed in a solution found in donor cell 4. Preferably, the wavelength of light reaching skin 6 is chosen not only to reduce damage to skin 6, but also to increase activity in donor cell 4 (e.g., 350 nm to 450 nm). The pulse rate of such light may also be between 1.7 cps and 120 cps (e.g., 24 cps). If fluorescent light is employed as light source 3, it preferably has a wavelength range from about 260 nm to about 760 nm. If ultraviolet, visible, near infrared, or halogen light is employed as light source 3, the light source preferably has a wavelength range from about 340 nm to about 900 nm. The invention is not limited to the these wavelengths.

Donor cell 4 holds a biologically active substance (e.g., chemicals, drugs, antibiotics, peptides, hormones, proteins, DNA, RNA and mixtures thereof). Donor cell 4 may also include a solvent that forms a solution with the biologically active substance. The solution may also include a photocatalytic (having, for example, a band gap energy of between about 2.9 eV and about 3.2 eV) and/or a gelling agent. The solvent may be an aqueous or an organic solvent. Furthermore, skin 6 may be a cellular surface which is an outer layer of a skin. Generally, skin 6 may be any medium that allows at least the biologically active portion of donor cell 4 to diffuse into that medium in response to that medium being exposed to light source 3. In one embodiment, this medium is a cell membrane for transmembrane delivery.

Clamp 5 is preferably included in testing device 100 to couple donor cell 4 and skin 6 to receiving cell 7. Receiving cell 7 may be present in container 17 as a result of diffusion of at least the biologically active portion of donor cell 4 through skin 6. Also, receiving cell 7 may contain a solvent, e.g., HPLC grade water, wherein diffusion of at least the biologically active portion of donor cell 4 through skin 6 enters into the solvent. Generally, the concentration of the biologically active substance is higher in donor cell 4 than in receiving cell 7. Skin supports 16 may also be included in order to position skin 6 above container 17 and below light source 3. Donor cell 4 is located in container 14 and preferably contacts an area of skin 6. Container 14 and container 17 may be the same container. Furthermore, a skin aperture (not shown) may exist to receive at least a portion of skin 6 such that skin 6 separates container 14 from container 17.

Temperature control device 8 is preferably applied to at least a portion of container 7. Temperature directors 18 may be included as a part of container 17 or coupled to container 17 to direct temperature control device 8. Temperature directors 18 may also be used to structurally provide support for a heat source such as a heat bath. For example, hot water may be placed in housing defined by temperature directors 18 and a portion of container 17 between temperature directors 18. Further to this example, a heat source may be used to heat such water. Alternatively, a heat source may be directly coupled to container 17. Preferably, temperature control device 8 heats container 17 to a constant level. While the temperature of the solvent in receiving cell 7 can vary, it is preferably about 37° C., human body temperature, or about 33.5° C., human skin surface temperature. For applications requiring container 17 to be cooled, temperature control device 8 may additionally or alternatively be a cooling source. A temperature sensor (not shown) may be placed in, on, or about container 17 or a heat source such that temperature control device 8 keeps container 17 at a particular temperature for a particular period of time.

Stir bar 9 may be included in container 17 to stir any solution in container 17. Preferably, stir bar 9 constantly stirs the solution in container 17. Container 17 may be alternatively stirred, for example, by a shaking device. Removal of stir bar 9 would, for example, allow container 17 to be easily sanitized while reducing the design complexity of container 17. Stir bar 9 may be connected to an electrical motor (not shown).

Port 10 may be included in container 17 to add or remove samples to or from receiving cell 7 or solutions to or from container 17. Generally, port 10 is an aperture in container 17. Guide tube 12 may form an extended port 10 such that a sample recovery or dispersal tool can easily migrate to port 10. Cover 13 may be employed on port 10 (or guide tube 12) such that contaminants from outside container 17 do not pass through port 10 when samples are being added or removed from container 17. Guide tube 12 is generally an adapter. For example, if the recovery/dispersal tool is a needle, then guide tube 10 preferably facilitates the coupling of the needle to port 10.

Lens 23 may be included in testing device 100 to, for example, focus light source 3 on donor cell 4 or to provide a transparent medium in which light from light source 3 may pass onto donor cell 4 while contaminants from outside container 14 are isolated from donor cell 4. Lens 23 may be a transparent medium, such as, for example, a transparent polymer or glass.

Container 17 may include insulation 15 to control the amount of heat supplied to container 17. Insulation 15 may also be part of a heat bath and may be filled with water. The amount of insulation 15 about temperature control device 8 may be reduced such that temperature control device 8 affects the temperature of container 17 more than ambient heat.

Figure 2:
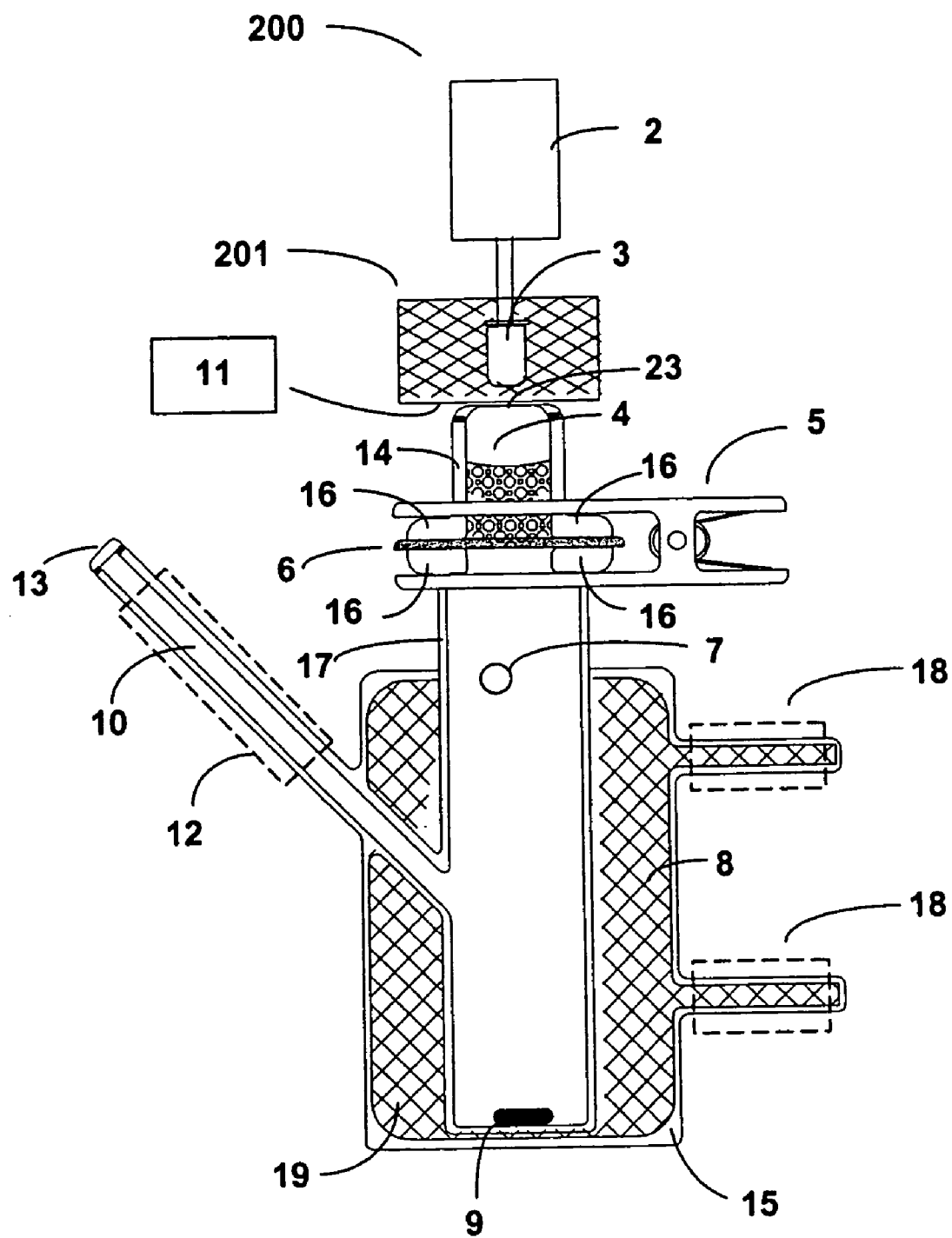
FIG. 2 shows a Franz skin diffusion device similar to that in FIG. 1 except the light source is embedded in an optically clear medium or light pad that does not absorb the wavelength emitted from the light source.

FIG. 2 illustrates testing device 200 in accordance with the invention. Testing device 200 includes light pad 201 and is otherwise similar/identical to testing device 100 of FIG. 1. Light pad 201 includes at least one and preferably more than one light source 3, which is preferably an LED. Light pad 201 is preferably fabricated from an optically clear material (e.g., poly(methyl methacrylate) or silicone rubber). Similar to testing device 100, testing device 200 can also be oriented differently than shown.

Figure 3A:
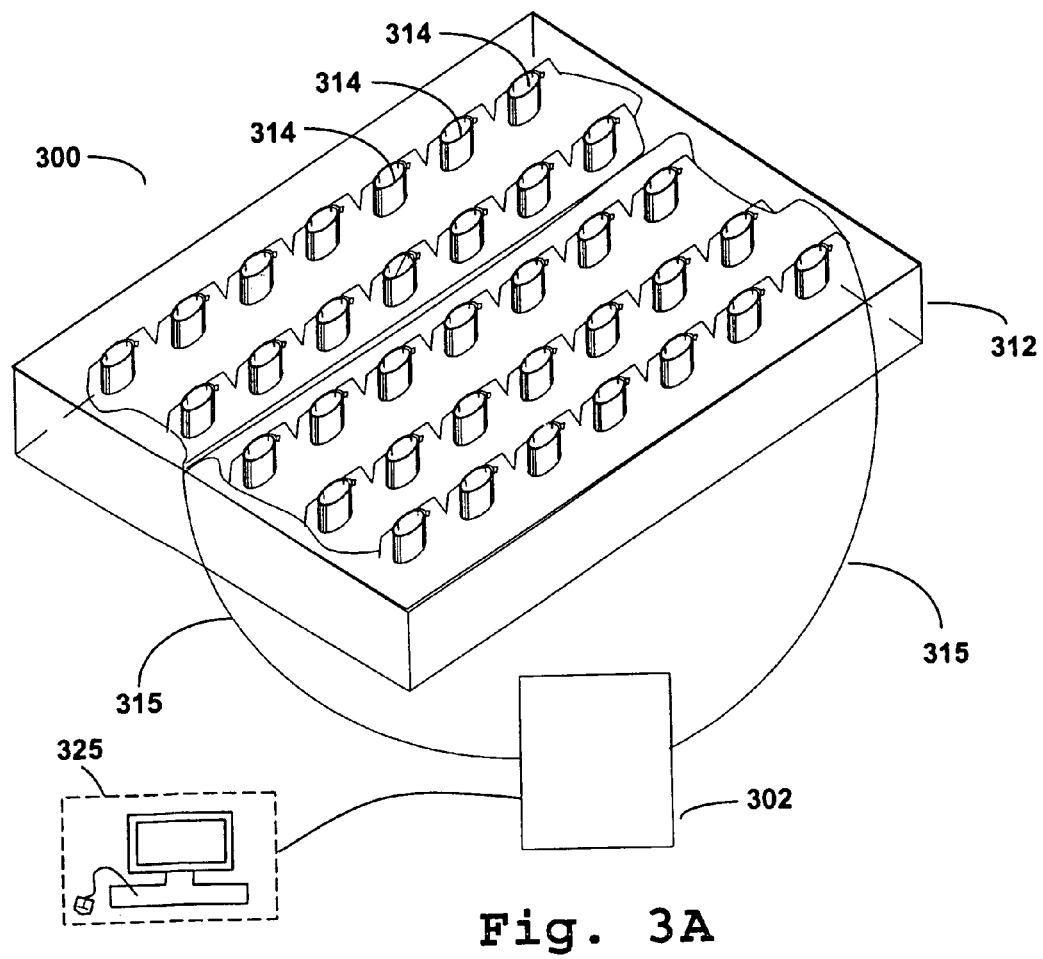
FIG. 3A shows an array of light sources embedded in an optically clear medium or light pad and electrically coupled to each other and to a control device or power supply.

FIG. 3A illustrates light pad 300 in accordance with the invention. Light pad 300 includes driver circuit 302, base 312, light source 314, and wiring 315. Wiring 315 may be included to electrically couple control device 302 (or a power supply) to one or more light sources 314, and wiring 315 may have a protective sheath. Base 312 is preferably a silicon substrate in which light sources 314 are fabricated. Light sources 314 are preferably incoherent sources of light and are preferably LEDs having a narrow bandwidth. Alternatively, other types of light sources may be used. Light sources 314 may be turned ON and OFF by driver circuit 302 either as a group, individually, or in sections. For example, light sources 314 may be arranged as multiple arrays of light sources. Driver circuit 302 may then selectively pulse only a single array of light sources 314 such that only a desired portion of a medium (e.g., skin 6 from FIGS. 1 and 2) receives pulsed light. Moreover, multiple arrays can be included on light pad 300 in which each array includes LEDs of a specific wavelength. Thus, when only a specific wavelength is desired or needed, driver circuit 302 can selectively turn ON the array comprised of LEDs having that particular wavelength. For example, light pad 300 may include an array of ILEDs and an array of LEDs where driver circuit 302 selectively switches between the ILED array and the LED array. This may be desirable when a biologically active substance is more reactive to or less degraded/denatured by light of a particular wavelength.

Instead of having arrays of particular wavelengths, other characteristics may be utilized. For example, two arrays may have LEDs of the same wavelength, but the arrays may be of different intensities or may focus light in different directions. Light sources 314 may be mounted on gears (not shown) that can be turned/rotated by motors (not shown) and controlled by driver circuit 302 such that the direction and intensity of light being provided to a particular area can be manipulated. Driver circuit 302 may be controlled by computer 325 either directly or via a graphical user interface (GUI).

Light pad 300 can be, for example, a tanning bed. If light pad 300 provided coherent light, a light scatter device, filter, or conversion device can be provided to convert the coherent light into incoherent light.

Figure 3B:
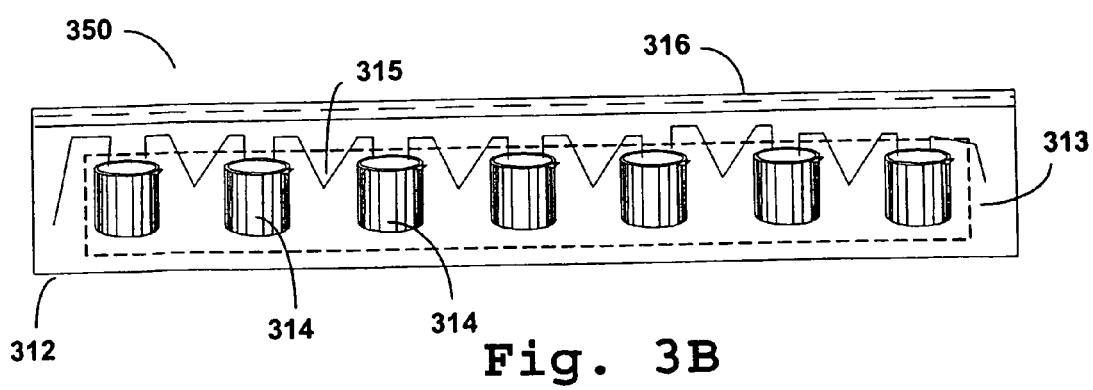
FIG. 3B illustrates multiple light sources electrically connected in series and embedded in an optically clear medium or light pad wherein the upper surface of the light pad is coated with a reflective layer and the lower surface of the light pad is optically clear.

FIG. 3B illustrates light array 313 mounted in base 312. Array 313 includes two or more light sources 314 electrically connected in series by wiring 315. If light sources 314 are to provide light below base 312, reflective layer 316 may be included above base 312 to reflect light scattered from base material or skin while base 312 remains a transparent medium. Multiple light sources 314 may have different wavelengths such that light sources 314 having a particular wavelength may be selectively turned ON and OFF to provide light of a single selected wavelength or multiple selected wavelengths. Light sources 314 may provide light above base 312. In this case, reflective layer 316 may be placed on base 312 (which does not have to be transparent) and beneath light sources 314 to reflect light above base 312. The reflective layer can be a wavelength specific reflective coating (e.g., aluminum, ZnO, silver or any reflective paint).

The methods and devices of the invention can also be used in combination with other active delivery techniques such as ionotophoresis, sonophoresis and microporation.

EXAMPLES

The following materials were used in the examples set forth below.

Materials

All biologically active compounds, including ascorbic acid, ascorbyl palmitate, pyridoxine, nicotinic acid, theobromine, theophylline, caffeine, nicotinamide, glycine-tyrosine (238 Da), valine-tyrosine-valine (380 Da), methionine enkephalin acetate (574 Da), leucine enkephalin (556 Da), angiotensin II acetate (1046 Da), β-estradiol (272 Da), methyl testosterone (303 Da), progesterone (315 Da) and bovine insulin (5,733 Da), lidocaine, amphotericin B, as well as Hank's balanced salt solution, were obtained from Sigma (St. Louis, Mo.). HPLC grade water, acetonitrile, citric acid, formic acid, trifluoroacetic acid (TFA) and isopropanol were purchased from either Fisher Scientific (Pittsburgh, Pa.) or Sigma. Rutile form of titanium dioxide (Ti-Pure® or Rutile Titanium Dioxide No. 754) was obtained from Dupont (Wilmington, Del.). Klucel® or hydroxypropyl cellulose was obtained from Hercules (Wilmington, Del.).

Theophylline-7 acetic acid was prepared from a 1:1 mole ratio of theophylline anhydrous to monochloro-acetic acid. The reaction was performed with a strict control of pH at 7 by adjusting solution with NaOH (50% w/v). The material was recrystallized twice from water and analyzed on HPLC for purity.

Franz skin cell consoles with synchronized stirrers were purchased from Crown Glass, N.J. and Perme Gear, Finland. Temperature control was modulated by an external circulating water bath.

Human cadaver split thickness skin (epidermis and dermis) frozen in nitrogen was obtained from the New York Firefighters Skin Bank and Shriners Hospitals for Children and used for the experiments described herein. Skin samples were supplied as 3" wide×10" length pieces and cut to 1 cm² sections prior to use on the Franz cell console. "Epidermis only" skin was also used for the experiments of this invention but these data are not reported herein. All skin was obtained from the leg or posterior torso skin of different female donors between the ages of 24 to 48 and the thicknesses of the dermis layer varied with each donor. Prior to use, the skin was stored at −40° C. and thawed in Hank's balanced salt solution at room temperature.

Sample Preparation and Analysis of Biologically Active Substances

Permeation tests were performed on viscous solutions containing a biologically active substance and a gelling agent or a biologically active substance, a photocatalyst and a gelling agent.

The biologically active compounds used in the permeation studies of this invention are listed in Table 1.

TABLE 1

Biologically Active Compounds Used in Permeation Studies

| Compound No. | Chemical Name[1] | Compound Classification |
|---|---|---|
| 1 | Theophylline-7 acetic acid | polar |
| 2 | Sodium ascorbyl phosphate | polar |
| 3 | Ascorbic Acid | polar |
| 4 | Ascorbyl palmitate | polar |
| 5 | Pyridoxine | polar |
| 6 | Nicotinic acid | slightly polar |
| 7 | Theobromine | non-polar |
| 8 | Theophylline | non-polar |
| 9 | Caffeine | non-polar |
| 10 | Nicotinamide | non-polar |
| 11 | Gly-Tyr | peptide |
| 12 | Val-Tyr-Val | peptide |
| 13 | Methionine Enkephalin Acetate (Tyr-Gly-Gly-Phe-Met) (SEQ ID NO: 1) | peptide/hormone |
| 14 | Leucine Enkephalin (Tyr-Gly-Gly-Phe-Leu) (SEQ ID NO: 2) | peptide/hormone |
| 15 | Angiotensin II Acetate (Asp-Arg-Val-Tyr-Ile-His-Pro-Phe) (SEQ ID NO: 3) | peptide/hormone |
| 16 | β-Estradiol | hormone |
| 17 | Methyl Testosterone | hormone |
| 18 | Progesterone | hormone |
| 19 | Insulin | hormone |
| 20 | Lidocaine | anaesthetic and cardiac depressant |
| 21 | Amphotericin B | antibiotic |

[1]Amino acids are designated as follows: glycine (Gly), tyrosine (Tyr), valine (Val), phenylalanine (Phe), methionine (Met), leucine (Leu), aspartic acid (Asp), arginine (Arg), isoleucine (Ile), histidine (His), and proline (Pro).

Characteristics of compounds in Table 1 are well-known in the art (Merck Index), some of which are listed in the following Table 2.

TABLE 2

Characteristics of Compounds

| Compound | Water Solubility (1 g) | pKa | pKb | Therapeutic Use | UV Max (nm) |
|---|---|---|---|---|---|
| 3 | 3 ml | | | Physiological antioxidant; coenzyme reactions; collagen synthesis; antimicrobial and antioxidant in foodstuffs; antiscorbutic | 245, 265 |
| 5 | 4.5 ml | | | Vitamin (enzyme cofactor), nutritional factor | 235, 290, 325 |
| 6 | 60 ml | 4.85 | | Antihyperlipoprotinemic, vitamin (enzyme cofactor) | 263 |
| 7 | 2000 ml | 10 | 14 | Diuretic, bronchodilator, cardiotonic | 274 |
| 8 | 120 ml | 8.77 | 11.5 | Bronchodilator | 274 |
| 9 | 46 ml | | | CNS, cardiac and respiratory stimulant, diuretic | 274 |
| 10 | 1 ml | | | Antiacne, vitamin (enzyme cofactor) | 261 |
| 16 | Insoluble | | | Estrogen | 225, 280 |

TABLE 2-continued

Characteristics of Compounds

| Compound | Water Solubility (1 g) | pKa | pKb | Therapeutic Use | UV Max (nm) |
|---|---|---|---|---|---|
| 17 | Insoluble | | | Androgen | 240 |
| 18 | Insoluble | | | Progesterone | 240 |
| 19 | | | | Regulates carbohydrate and lipid metabolism, influences protein synthesis, antidiabetic | |

Different reversed phase high performance liquid chromatography (RP-HPLC) methods were developed for analyzing groups of the above-identified biologically active substances or compounds. These groups are identified as follows:

| Group I: | theophylline, theobromine, theophylline-7-acetic acid and caffeine; |
| Group II: | ascorbic acid, ascorbyl palmitate, and sodium ascorbyl phosphate; |
| Group III: | ascorbic acid, pyridoxine, nicotinic acid and nicotinamide; |
| Group IV: | gly-tyr, val-tyr-val, methionine enkephalin acetate, leucine enkephalin and angiotensin II acetate; |
| Group V: | β-estradiol, progesterone and methyl testosterone; and |
| Group VI: | insulin; |
| Group VII: | lidocaine; and |
| Group VIII: | amphotericin B. |

Example 1

Preparation and analysis of Group I solutions. RP-HPLC was performed on a Bodman Industries HPLC system equipped with a C18, 4.6×150 mm, 5 µm Lichrosorb column, LabAlliance Series II and III model pumps, a 200-1100 nm UV-VIS detector and a DStar autosampler (Bodman Industries, Aston, Pa.). Group I biologically active samples were dissolved in HPLC grade water to give a final concentration of 0.5% (w/v). Elution profiles were monitored at 274 nm in a mobile phase comprising 10% (v/v) acetonitrile in HPLC water using an isocratic method. Samples were run over a period of 9 minutes at a flow rate of 1 ml/min. Data was analyzed using DataAlly (Bodman Industries, Aston, Pa.). All peaks were baseline resolved.

For permeation studies, Group I biologically active substances were prepared by either one of two methods: (a) the substances were dissolved in HPLC grade water to yield a final concentration of 0.5% (w/v) before heating to 70° C. until dissolved; or (b) the substances were dissolved in HPLC grade water to yield a final concentration of 0.5% (w/v) at room temperature. One percent (w/v) hydroxypropyl cellulose was then added to the solution and the total solution was halved. To the second half of the solution, 2% (w/w) of the rutile form of $TiO_2$ was dispersed in the viscous solution containing the biologically active substance and hydroxypropyl cellulose using a homomixer at 3000 rpm.

Example 2

Preparation and analysis of Group II solutions. RP-HPLC was performed on a Bodman Industries HPLC system equipped with a C18, 4.6×250 mm, 5 µm Alltech Econosphere column (Fisher, Pittsburgh, Pa.), LabAlliance Series II and III model pumps, a 200-1100 nm UV-VIS detector and a DStar autosampler (Bodman Industries, Aston, Pa.). Group II biologically active samples were dissolved in HPLC grade water to give a final concentration of 1% (w/v). Elution profiles were monitored at 245 nm in a mobile phase comprising 4:1 ratio of acetonitrile to 12.5 mM citric acid in HPLC grade water using an isocratic method. Samples were run at a flow rate of 2 ml/min. Data was analyzed using DataAlly (Bodman Industries, Aston, Pa.). All peaks were baseline resolved.

For permeation studies, Group II biologically active substances were prepared by dissolving the substance in HPLC grade water to yield a final concentration of 1.0% (w/v). One percent (w/v) hydroxypropyl cellulose was then added to the solution and the total solution was halved. To the second half of the solution, 2% (w/w) of the rutile form of $TiO_2$ was dispersed in the viscous solution containing the biologically active substance and hydroxypropyl cellulose using a homomixer at 3000 rpm.

Example 3

Preparation and analysis of Group III solutions. RP-HPLC was performed on a Bodman Industries HPLC system equipped with a C18, 4.6×250 mm, 5 µm Vydac 201SP54 column (Vydac, Hesperia, Calif.), a LabAlliance Series II or III model pump, a 200-1100 nm UV-VIS detector and a DStar autosampler (Bodman Industries, Aston, Pa.). Group III biologically active samples were dissolved in 0.1 M potassium acetate in HPLC grade water to give a final concentration of 0.5% (w/v). Elution profiles were monitored at 245 nm using a gradient method wherein the mobile phase A comprised 0.1 M potassium acetate in HPLC grade water (pH adjusted to 4.9 to 5.2 using formic acid) and mobile phase B comprised 50% (v/v) acetonitrile in HPLC grade water. A 5% to 60% gradient of mobile phase B was run over a period of 15 minutes at a flow rate of 1.5 ml/min. Data was analyzed using DataAlly (Bodman Industries, Aston, Pa.). All peaks were baseline resolved.

For permeation studies, Group III biologically active substances were prepared by dissolving the substance in HPLC-grade water to yield a final concentration of 0.5% (w/v). One percent (w/v) hydroxypropyl cellulose was then added to the solution and the total solution was halved. To the second half of the solution, 2% (w/w) of the rutile form of $TiO_2$ was dispersed in the viscous solution containing the biologically active substance and hydroxypropyl cellulose using a homomixer at 3000 rpm.

Example 4

Preparation and analysis of Group IV solutions. RP-HPLC was performed on a Bodman Industries HPLC system equipped with a C18, 4.6×250 mm, 5 µm Vydac 218TP54 column (Vydac, Hesperia, Calif.), a LabAlliance Series II or III model pump, a 200-1100 nm UV-VIS detector and a DStar autosampler (Bodman Industries, Aston, Pa.). Group IV biologically active samples were dissolved in HPLC grade water to give a final concentration of 2 mg/ml gly-tyr, 1 mg/ml val-tyr-val, 1 mg/ml methionine enkephaline acetate, 1 mg/ml leucine enkephalin and 0.5 mg/ml angiotensin II acetate. Elution profiles were monitored at 215 nm using a gradient method wherein the mobile phase A comprised a 5:95 ratio of acetonitrile to HPLC grade water containing 0.1% (v/v) TFA and mobile phase B comprised a 75:25 ratio of acetonitrile to HPLC grade water containing 0.1% (v/v)

TFA. A 5% to 30% gradient of mobile phase B was run over a period of 45 minutes at a flow rate of 1 ml/min. Data was analyzed using DataAlly (Bodman Industries, Aston, Pa.). All peaks were baseline resolved.

For permeation studies, Group IV biologically active substances were prepared by dissolving the substance in HPLC grade water to yield final concentrations of 2 mg/ml gly-tyr, 1 mg/ml val-tyr-val, 1 mg/ml methionine enkephaline acetate, 1 mg/ml leucine enkephalin and 0.5 mg/ml angiotensin II acetate. One percent (w/w) hydroxypropyl cellulose was then added to the solution and the total solution was halved. To the second half of the solution, 2% (w/w) of the rutile form of $TiO_2$ was dispersed in the viscous solution containing the biologically active substance and hydroxypropyl cellulose using a homomixer at 3000 rpm.

Example 5

Preparation and analysis of Group V solutions. RP-HPLC was performed on a Bodman Industries HPLC system equipped with a C18, 4.6×250 mm, 5 µm Zorbax column (Fisher, Pittsburgh, Pa.), a LabAlliance Series II or III model pump, a 200-1100 nm UV-VIS detector and a DStar autosampler (Bodman Industries, Aston, Pa.). Group V biologically active samples were dissolved in HPLC grade water to give a final concentration of 0.5% (w/v). Elution profiles were monitored at 226 nm using an isocratic method wherein the mobile phase comprised 30% (v/v) isopropanol in HPLC grade water at a flow rate of 1 ml/min. Data was analyzed using DataAlly (Bodman Industries, Aston, Pa.). All peaks were baseline resolved.

For permeation studies, Group V biologically active substances were prepared by dissolving the substance in HPLC grade water to yield a final concentration of 0.5% (w/v). One percent (w/v) hydroxypropyl cellulose was then added to the solution and the total solution was halved. To the second half of the solution, 2% (w/w) of the rutile form of $TiO_2$ was dispersed in the viscous solution containing the biologically active substance and hydroxypropyl cellulose using a homomixer at 3000 rpm.

Example 6

Preparation and analysis of Group VI solution. RP-HPLC was performed on a Bodman Industries HPLC system equipped with a C4, 4.6×250 mm, 5 µm Vydac 214TP54 column (Vydac, Hesperia, Calif.), a LabAlliance Series II or III model pump, a 200-1100 nm UV-VIS detector and a DStar autosampler (Bodman Industries, Aston, Pa.). Group VI biologically active samples were dissolved in HPLC grade water to give a final concentration of 1 mg/ml. Elution profiles were monitored at 232 nm using a isocratic method wherein the mobile phase comprised 30% (v/v) acetonitrile in HPLC grade water with 0.1% (v/v) TFA added. The samples were run at a flow rate of 1 ml/min. Data was analyzed using DataAlly (Bodman Industries, Aston, Pa.). All peaks were baseline resolved.

For permeation studies, Group VI biologically active substances were prepared by dissolving 1 mg/ml (activity=27.83 units/mg) of the substance in HPLC grade water. One percent (w/v) hydroxypropyl cellulose was then added to the solution and the total solution was halved. To the second half of the solution, 2% (w/w) of the rutile form of $TiO_2$ was dispersed in the viscous solution containing the biologically active substance and hydroxypropyl cellulose using a homomixer at 3000 rpm.

Example 7

Preparation and analysis of Group VII solutions. RP-HPLC was performed on a Bodman Industries HPLC system equipped with a C18, 4.6×250 mm, 5 µm Vydac 218TP54 column (Vydac, Hesperia, Calif.), a LabAlliance Series I model pump, a 200-1100 nm UV-VIS detector. Group VII biologically active samples were dissolved in HPLC grade water to give a final concentration of 1.0% (w/v). Elution profiles were monitored at 215 nm using a isocratic method wherein the mobile phase comprised 28% (v/v) acetonitrile and 0.1% TFA in HPLC grade water at a flow rate of 1 ml/min. Data was analyzed using DataAlly (Bodman Industries, Aston, Pa.). All peaks were baseline resolved.

For permeation studies, Group VII biologically active substances were prepared by dissolving 1 g of the substance in 100 ml HPLC grade water. One percent (w/v) hydroxypropyl cellulose was then added to the solution and the total solution was halved. To the second half of the solution, 2% (w/w) of the rutile form of $TiO_2$ was dispersed in the viscous solution containing the biologically active substance and hydroxypropyl cellulose.

Example 8

Preparation and analysis of Group VIII solutions. RP-HPLC was performed on a Bodman Industries HPLC system equipped with a C18, 4.6×250 mm, 5 µm Vydac 201SP54 column (Vydac, Hesperia, Calif.), a LabAlliance Series I model pump, a 200-1100 nm UV-VIS detector. Group VIII biologically active samples were dissolved in HPLC grade water to give a final concentration of 1 mg/ml. Elution profiles were monitored at 405 nm using a isocratic method wherein the mobile phase comprised 40% (v/v) acetonitrile in HPLC grade water, pH adjusted to 3.8 using glacial acetic acid, at a flow rate of 1 ml/min. Data was analyzed using DataAlly (Bodman Industries, Aston, Pa.). All peaks were baseline resolved.

For permeation studies, Group VIII biologically active substances were prepared by dissolving the substance in HPLC grade water. One percent (w/v) hydroxypropyl cellulose was then added to the solution and the total solution was halved. To the second half of the solution, 2% (w/w) of the rutile form of $TiO_2$ was dispersed in the viscous solution containing the biologically active substance and hydroxypropyl cellulose.

Example 9

Conditions used to test transdermal delivery of biologically active substances on human cadaver skin. Table 3 below identifies the conditions, along with corresponding abbreviations, used in the measurement of percutaneous absorption for compounds listed in Table 1.

Because ambient incoherent fluorescent light is present in most artificially illuminated and natural environments, the influence of ambient incoherent fluorescent light on transdermal delivery was tested and identified as "controls" in Table 3 below (see descriptions for Ctrl, Ctrl-$TiO_2$, Dark and Dark-$TiO_2$ in Table 3). In order to produce conditions where ambient light was absent, samples were shielded with aluminum foil.

The experiments were run by placing a solution containing the biologically active substance in the donor cell of the Franz device directly on contact with the cadaver donor "split thickness skin," separating the donor cell and the receiving cell. To test active transport, the solution was either illuminated by pulsed incoherent light from the environment or supplied by an electrical source equipped with one or more LEDs. Variables tested for active transport included wavelength, pulse rate, duty cycle, addition of photocatalytic agent and time. Percutaneous absorption values were reported in units of microgram per square area per hour of donor/receptor cell exposed to light. These data are reported in Examples 10-21 included herein.

TABLE 3

Abbreviations and Experimental Conditions

| Abbreviation | Description and Experimental Conditions |
|---|---|
| Ctrl | Control, ambient light only (cool fluorescent light at 35 candela), wavelength range 260 nm to 750 nm, 120 cycles per second, 50% duty cycle |
| Ctrl-TiO$_2$ | Control, sample contained 2% (w/w) Rutile titanium dioxide, ambient light only (cool fluorescent light at 35 candela), wavelength range 260 nm to 750 nm, 120 cycles per second, 50% duty cycle |
| Day | Natural daylight control, Franz skin diffusion device placed next to window, light is not pulsed |
| Day-TiO$_2$ | Natural daylight control, sample contained 2% (w/w) Rutile titanium dioxide, Franz skin diffusion device placed next to window, light is not pulsed |
| Dark | Dark control, ambient light absent |
| Dark-TiO$_2$ | Dark control, sample contained 2% (w/w) Rutile titanium dioxide, ambient light absent |
| +TiO$_2$ | Sample contained contained 2% (w/w) Rutile titanium dioxide |
| 350 | 350 nm LED (350 nm ± 15 nm, 50% rated output, 30 µW), ambient fluorescent light absent |
| 390 | 390 nm LED (390 nm ± 10 nm, 50% rated output, 25 mW), ambient fluorescent light absent |
| 405 | 405 nm LED (405 nm ± 21 nm, 50% rated output, 290 millicandela), ambient fluorescent light absent |
| 450 | 450 nm LED (450 nm ± 10 nm, 50% rated output, 250 millicandela), ambient fluorescent light absent |
| 1.7 cps | 1.7 cycles per second, 66% duty cycle, on 0.42 seconds and off 0.15 seconds |
| 8.0 cps | 8.0 cycles per second, 50% duty cycle, on 0.0625 seconds and off 0.0625 seconds |
| 9.7 cps | 9.7 cycles per second, 74% duty cycle, on 0.076 seconds and off 0.027 seconds |
| 24 cps | 24 cycles per second, 75% duty cycle, on 0.032 seconds and off 0.010 seconds |
| 80 cps | 80 cycles per second, 50% duty cycle, on 0.00625 seconds and off 0.00625 seconds |

Example 10

Figure 4:
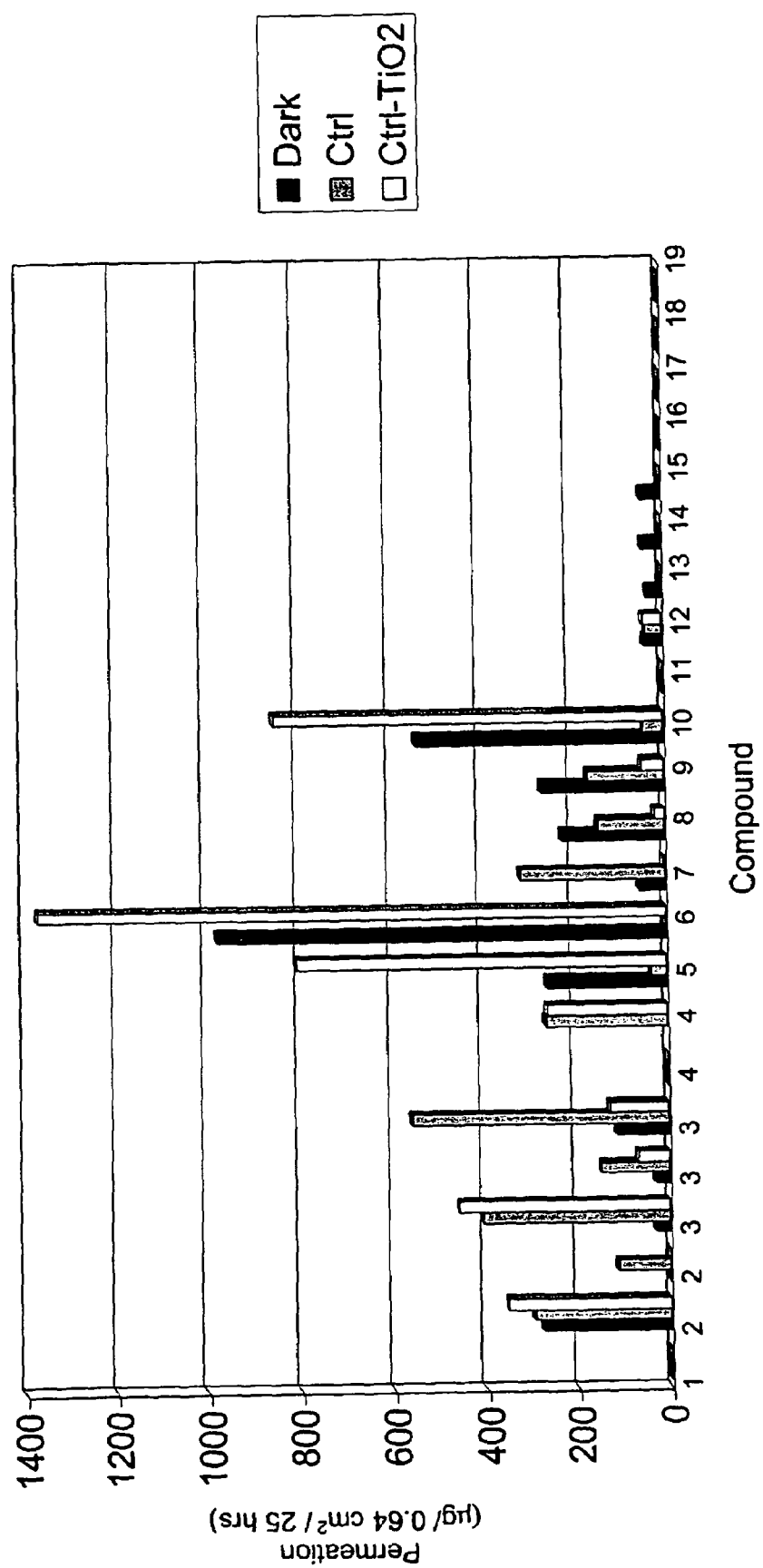
FIG. 4 illustrates the amount of a compound transported across intact human partial thickness skin over 25 hours in the presence and absence of ambient light. See Example 10.

Effect of ambient light on transdermal delivery of various compounds. Percutaneous absorption of compounds 1-19 listed in Table 1 were tested under Dark, Ctrl and Ctrl-TiO$_2$ conditions (see FIG. 4). These data demonstrate baseline permeation of the above-identified compounds in the absence and presence of ambient fluorescent light. In some compounds, the ambient fluorescent light from the laboratory ceiling lights had a significant effect on the permeation of, for example, compounds 3 and 7. In addition, 2% (w/w) TiO$_2$ can also have a significant effect on the permeation of the compounds (see compounds 5, 6 and 10). FIG. 4 also illustrates that compounds 11-19, which are peptides, hormones or proteins, are not significantly permeated in the absence or presence of ambient light or in the presence of TiO$_2$ and ambient light.

Two sets of data were reported for compounds 2 and 4 and three sets of data were reported for compound 3. The differences in permeation of similar samples can result from a number of factors. For example, the dermis layer of the split thickness skin can vary from donor to donor. If the dermis layer is particularly thin due to age, treatment over time, etc., a hole may form or be present during testing or the pulsed light may be directed at a transappendage such as a hair follicle, sebaceous gland and sweat ducts, allowing a rapid permeation of the biologically active agent under test conditions.

TABLE 4

Comparison of Transdermal Delivery of Skin Compounds Measured in the Absence and Presence of Ambient Light

| Compound No. | Permeation Dark (µg/0.64 cm$^2$/25 hrs) | Permeation Ctrl (µg/0.64 cm$^2$/25 hrs) | Permeation Ctrl-TiO$_2$ (µg/0.64 cm$^2$/25 hrs) |
|---|---|---|---|
| 1 | 0.00 | 0.00 | 0.00 |
| 2 | 274.40 | 295.20 | 351.40 |
| 2 | 0.00 | 110.50 | 0.00 |
| 3 | 30.90 | 404.10 | 456.30 |
| 3 | 30.90 | 147.40 | 67.01 |
| 3 | 110.50 | 557.90 | 127.20 |
| 4 | 0.00 | 0.00 | 0.00 |
| 4 | | 263.40 | 260.70 |
| 5 | 261.30 | 32.90 | 806.20 |
| 6 | 976.30 | 0.00 | 1371.00 |
| 7 | 54.39 | 317.40 | 4.27 |
| 8 | 224.10 | 144.90 | 23.04 |
| 9 | 269.40 | 168.70 | 47.22 |
| 10 | 543.70 | 42.72 | 851.80 |
| 11 | 0.00 | 0.00 | 0.00 |
| 12 | 37.24 | 35.26 | 41.18 |
| 13 | 31.56 | 0.00 | 0.00 |
| 14 | 41.68 | 0.00 | 0.00 |
| 15 | 42.80 | 0.00 | 0.00 |
| 16 | 0.00 | 0.00 | 0.00 |
| 17 | 0.00 | 0.00 | 0.00 |
| 18 | 0.00 | 0.00 | 0.00 |
| 19 | 1.12 | 3.55 | 0.00 |

Example 11

Figure 5:
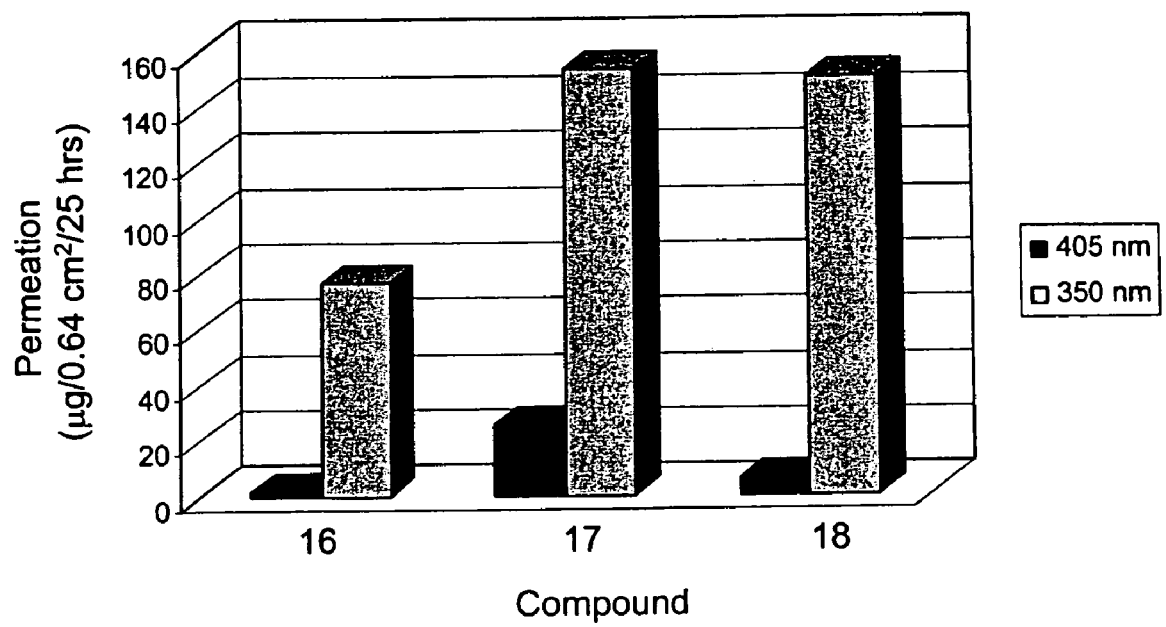
FIG. 5 illustrates the effect of wavelength on transdermal delivery of hormones at a pulse rate of 24 cycles per second (cps). See Example 11.

Table 5 and FIG. 5 illustrate permeation of hormones at a pulse rate of 24 cps at either 350 nm or 405 nm wavelength. These data demonstrate that hormones permeate to a greater extent at 350 nm at 24 cps with a 75% duty cycle than to 405 nm at 24 cps with a 75% duty cycle.

TABLE 5

Effect of Wavelength on Transdermal Delivery of Hormones at a Pulse Rate of 24 cps

| Compound No. | Permeation 405 (µg/0.64 cm$^2$/25 hrs) | Permeation 350 (µg/0.64 cm$^2$/25 hrs) |
|---|---|---|
| 16 | 2.25 | 76.58 |
| 17 | 25.37 | 153.25 |
| 18 | 6.19 | 149.91 |

Example 12

Figure 6:
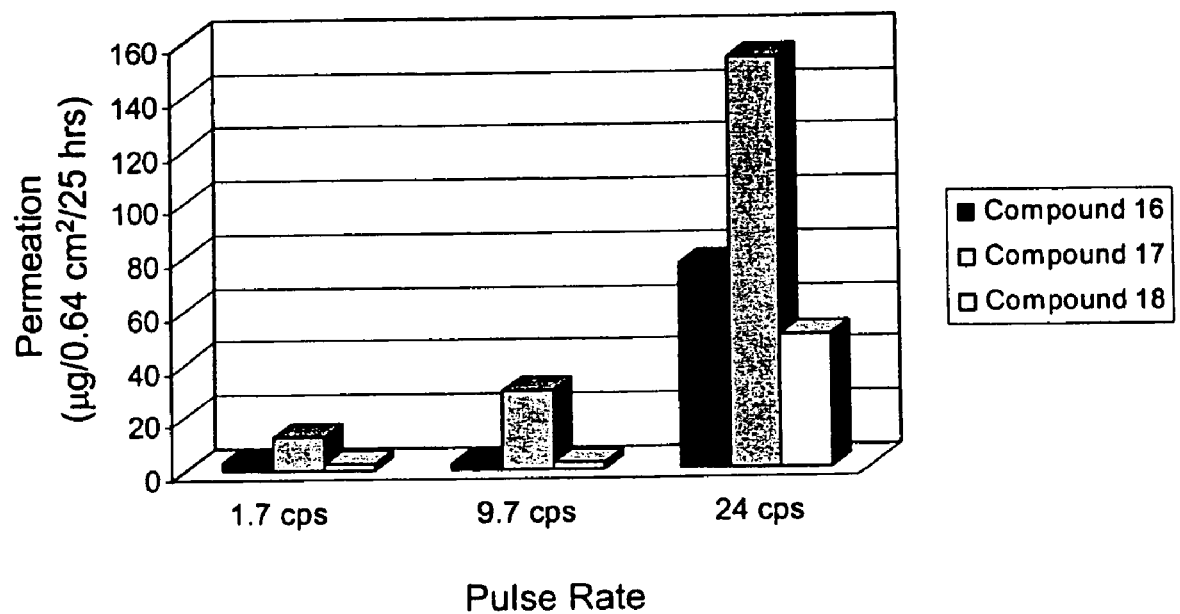
FIG. 6 illustrates the effect of pulse rate on transdermal delivery of hormones at different pulse rates. See Example 12.

Table 6 and FIG. 6 show permeation of hormones at 350 nm with a pulse rate of 1.7 cps, 9.7 cps or 24 cps. These data illustrate that a pulse rate of 24 cps has a more significant effect on permeation of hormones 16, 17 and 18 than pulse rates of 1.7 and 9.7 cps.

TABLE 6

Effect of Pulse Rate on Transdermal Delivery of Hormones at Different Pulse Rates

| Compound No. | Permeation 1.7 cps ($\mu g/0.64\ cm^2/25\ hrs$) | Permeation 9.7 cps ($\mu g/0.64\ cm^2/25\ hrs$) | Permeation 24 cps ($\mu g/0.64\ cm/25\ hrs$) |
|---|---|---|---|
| 16 | 3.69 | 2.85 | 76.58 |
| 17 | 12.84 | 29.57 | 153.25 |
| 18 | 2.58 | 2.80 | 49.91 |

Example 13

Figure 7:
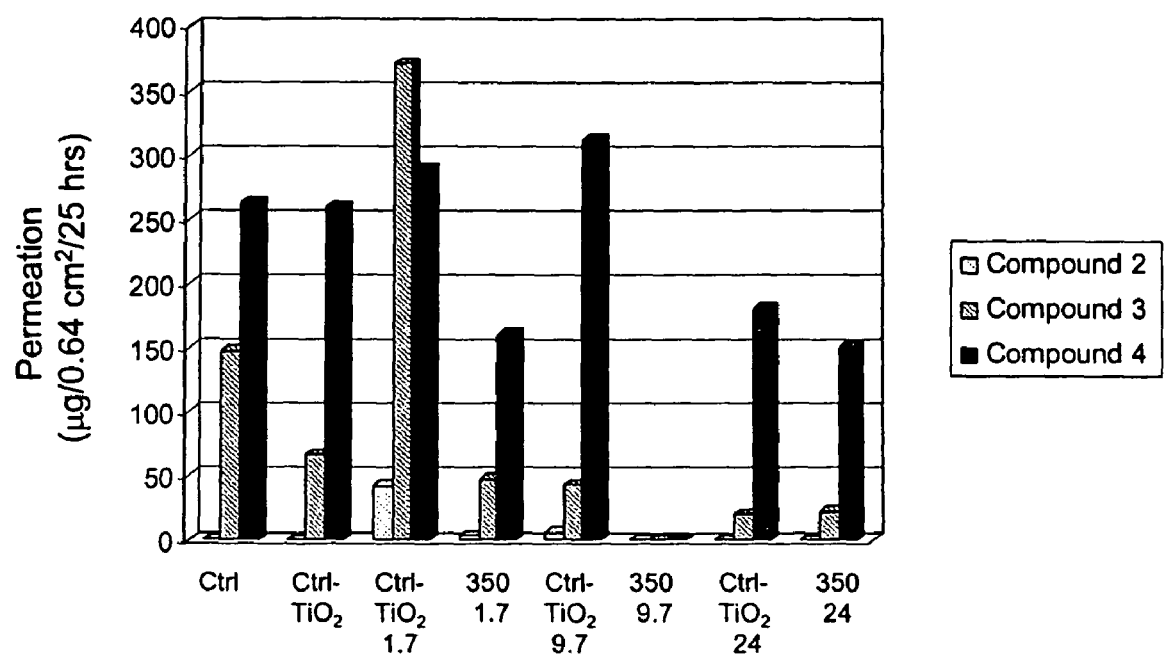
FIG. 7 illustrates the effect of photocatalytic agent and pulse rate on transdermal delivery of vitamin C and derivatives at 350 nanometers (nm). See Example 13.

Table 7 and FIG. 7 illustrate the effect of 2% $TiO_2$ and pulse rate on the permeation of vitamins at 350 nm. Addition of 2% $TiO_2$ increased the permeability of vitamin C and its derivatives when pulsed incoherent light was used. The result obtained for compound 3, ascorbic acid, is of particular interest because this compound is not readily permeated by transdermal delivery methods. Here, the addition of 2% $TiO_2$ at 1.7 cps caused enhanced permeation.

TABLE 7

Effect of Photocatalytic Agent and Pulse Rate on Transdermal Delivery of Vitamin C and Its Derivatives at 350 nm

| Comp. No. | Ctrl | Ctrl-$TiO_2$ | Ctrl-$TiO_2$/1.7 | 350/1.7 | Ctrl-$TiO_2$/9.7 | 350/9.7 | Ctrl-$TiO_2$/24 | 350/24 |
|---|---|---|---|---|---|---|---|---|
| 2 | 0.00 | 0.00 | 42.75 | 3.33 | 6.48 | 0.00 | 0.00 | 0.00 |
| 3 | 147.49 | 67.01 | 371.32 | 47.95 | 44.22 | 0.00 | 20.25 | 22.82 |
| 4 | 263.48 | 260.00 | 289.57 | 160.87 | 312.06 | 0.00 | 180.88 | 151.00 |

Example 14

Figure 8:
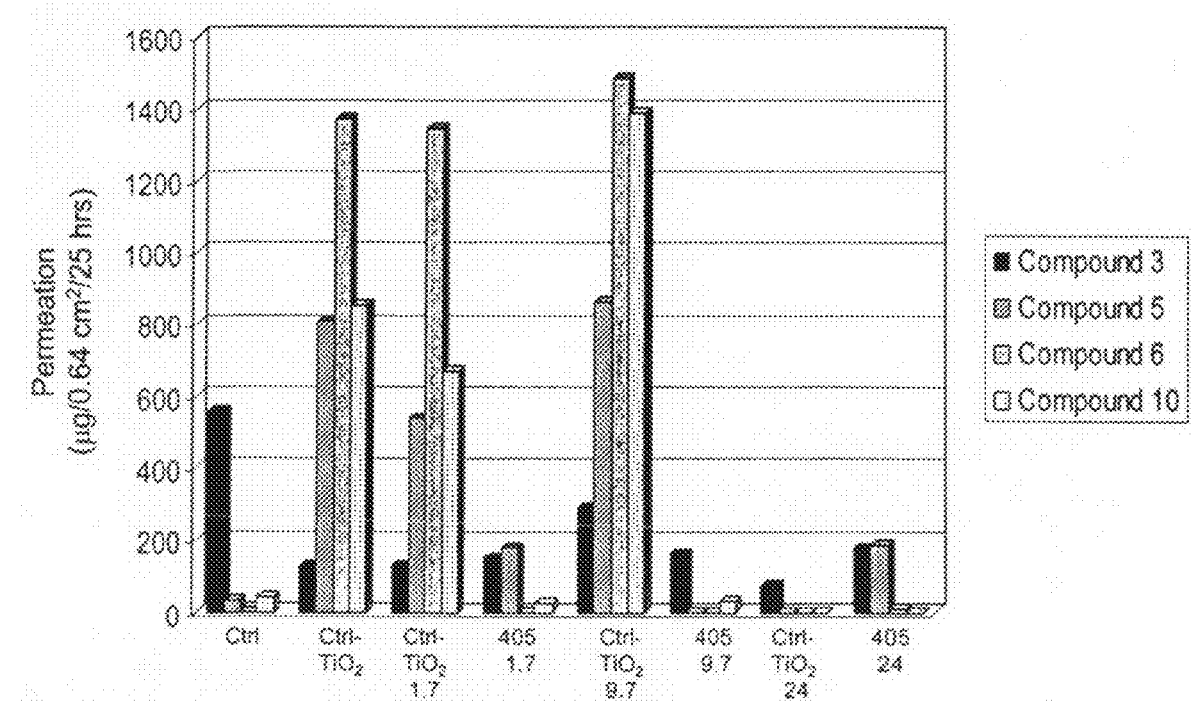
FIG. 8 illustrates the effect of photocatalytic agent and pulse rate on transdermal delivery of vitamins at 405 nm. See Example 14.

Table 8 and FIG. 8 illustrate the effect of $TiO_2$ and pulse rate on the permeation of vitamins at 405 nm. Transdermal delivery of compounds 5, 6 and 10 are enhanced with $TiO_2$, especially in Ctrl, 1.7 and 9.7 cps samples. In comparing FIGS. 7 and 8, compound 3 permeated the skin sample to a greater extent at 1.7 cps and 350 nm than at 9.7 cps and 405 nm.

TABLE 8

Effect of Photocatalytic Agent and Pulse Rate on Transdermal Delivery of Vitamins at 405 nm

| Comp. No. | Ctrl | Ctrl-$TiO_2$ | Ctrl-$TiO_2$/1.7 | 405/1.7 | Ctrl-$TiO_2$/9.7 | 405/9.7 | Ctrl-$TiO_2$/24 | 405/24 |
|---|---|---|---|---|---|---|---|---|
| 3 | 557.96 | 127.25 | 131.47 | 152.76 | 287.62 | 164.03 | 76.49 | 179.88 |
| 5 | 32.90 | 806.25 | 537.60 | 179.38 | 862.75 | 0.00 | 0.00 | 187.81 |
| 6 | 0.00 | 1371.00 | 1341.43 | 0.00 | 1481.09 | 0.00 | 0.00 | 10.61 |
| 10 | 42.72 | 851.83 | 668.31 | 26.22 | 1387.33 | 32.69 | 0.00 | 0.00 |

Example 15

Figure 9:
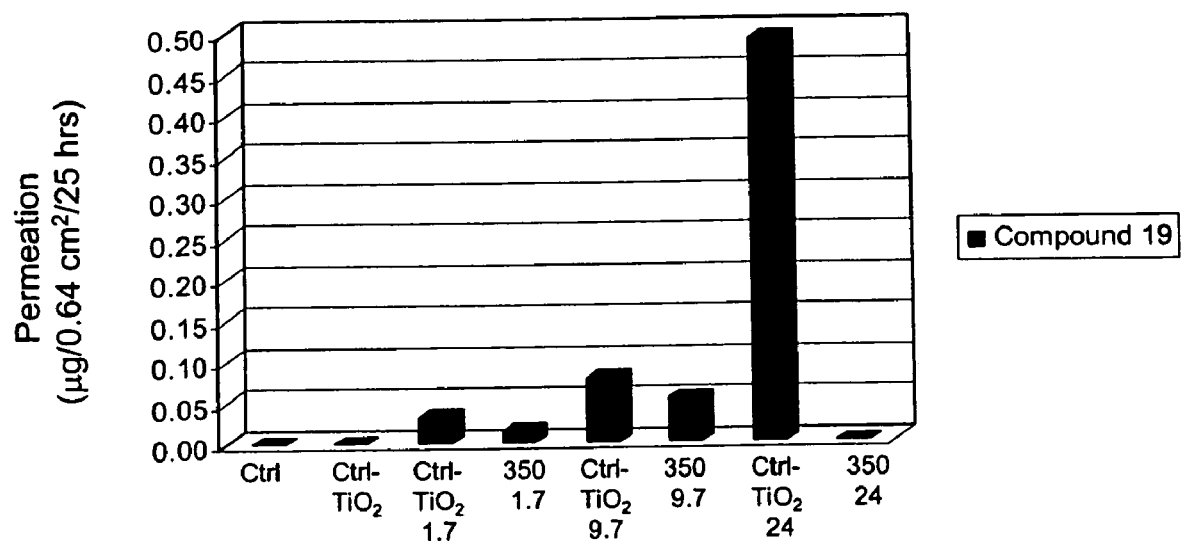
FIG. 9 illustrates the effect of photocatalytic agent and pulse rate on transdermal delivery of insulin at 350 nm. See Example 15.

Table 9 and FIG. 9 demonstrate the effect of $TiO_2$ and pulse rate on the permeation of compound 19, insulin, at 350 nm. In all cases, the $TiO_2$ enhanced delivery of insulin permeation. This data is significant because the molecular weight of insulin is 5,733, a weight that is typically too high for successful transdermal delivery.

TABLE 9

Effect of Photocatalytic Agent and Pulse Rate on Transdermal Delivery of Insulin at 350 nm

| Comp. No. | Ctrl | Ctrl-$TiO_2$ | Ctrl-$TiO_2$/1.7 | 350/1.7 | Ctrl-$TiO_2$/9.7 | 350/9.7 | Ctrl-$TiO_2$/24 | 350/24 |
|---|---|---|---|---|---|---|---|---|
| 19 | 0.000 | 0.000 | 0.033 | 0.014 | 0.078 | 0.054 | 0.490 | 0.000 |

Example 16

Figure 10:
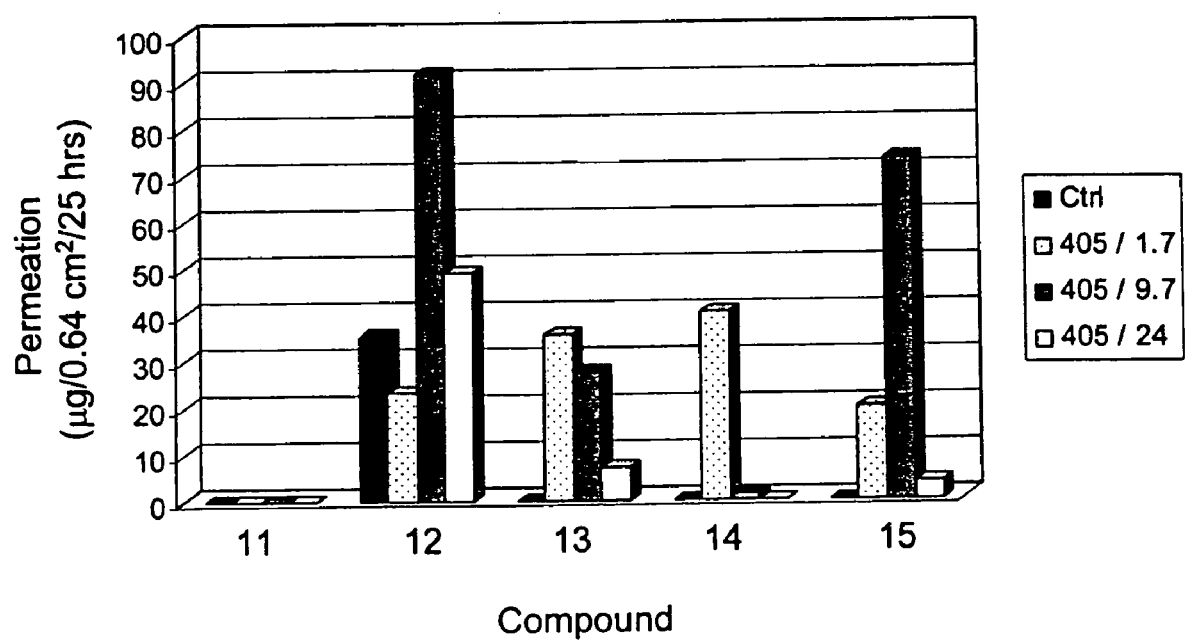
FIG. 10 illustrates the effect of pulse rate on transdermal delivery of peptides at 405 nm. See Example 16.

Table 10 and FIG. 10 illustrate the effect of pulse rate on the permeation of peptides at 405 nm. It was noted that the smallest peptide, compound 11, did not penetrate at any pulse rate used herein whereas the other peptides showed increased in permeation at certain pulse rates, for example, compound 12 at 9.7 cps, compound 12 at 1.7 cps and compound 14 at 1.7 cps.

TABLE 10

Effect of Pulse Rate on Transdermal Delivery of Peptides at 405 nm

| Compound | Ctrl | 405/1.7 | 405/9.7 | 405/24 |
|---|---|---|---|---|
| 11 | 0.00 | 0.00 | 0.00 | 0.00 |
| 12 | 35.26 | 23.21 | 91.68 | 48.83 |

TABLE 10-continued

Effect of Pulse Rate on Transdermal Delivery of
Peptides at 405 nm

| Compound | Ctrl | 405/1.7 | 405/9.7 | 405/24 |
|---|---|---|---|---|
| 13 | 0.00 | 35.47 | 27.57 | 6.86 |
| 14 | 0.00 | 40.38 | 1.23 | 0.00 |
| 15 | 0.00 | 19.99 | 73.19 | 3.87 |

Example 17

Figure 11A:
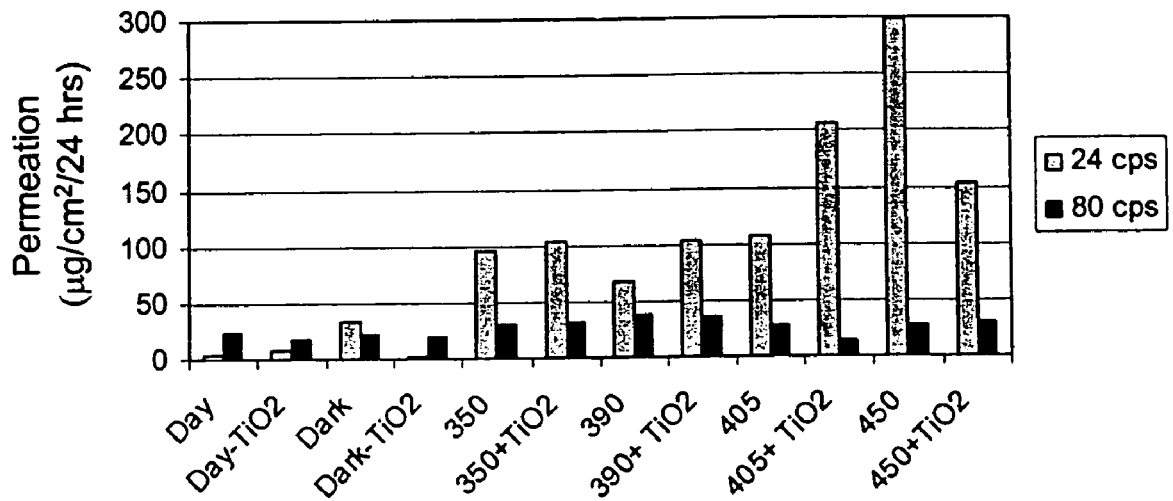
FIG. 11A illustrates the effect of wavelength, photocatalytic agent and pulse rate on transdermal delivery of methionine enkephalin acetate. See Example 17.
Figure 11B:
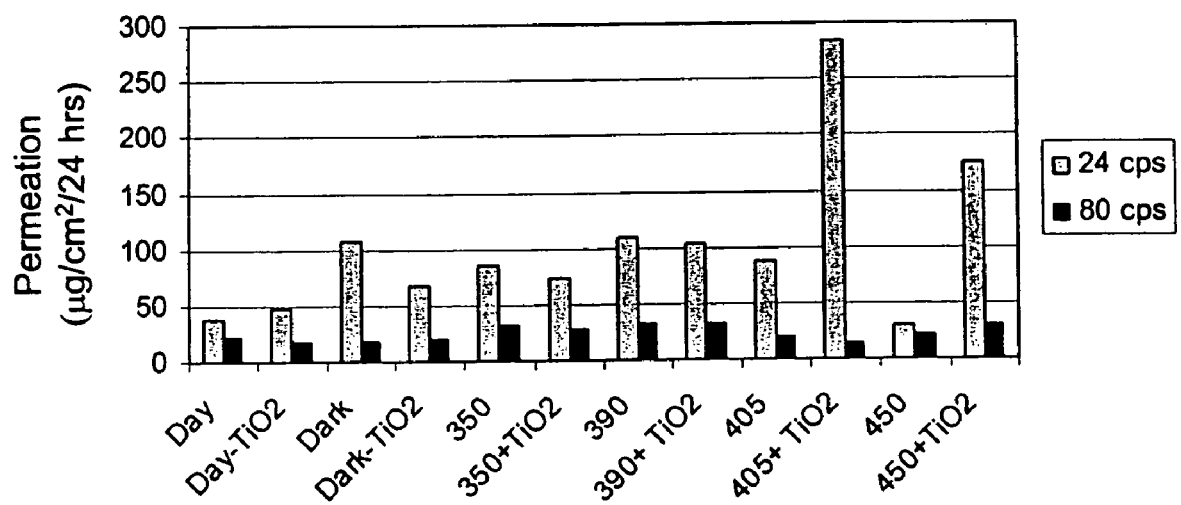
FIG. 11B illustrates the effect of wavelength, photocatalytic agent and pulse rate on transdermal delivery of leucine enkephalin. See Example 17.

Effect of wavelength, photocatalytic agent and pulse rate on transdermal delivery of Enkephalins. The permeation of methionine enkephalin acetate (compound 13 from Table 1) and leucine enkephalin (compound 14 from Table 1) were tested under various conditions, including wavelength, photocatalytic agent and pulse rate. Table 11 and FIGS. 11A and 11B illustrate permeation of compounds 13 and 14, respectively, under these various conditions. Note that each sample was tested in duplicate and the average value was reported for each condition tested (see Table 11). These data demonstrate that a pulse rate of 24 cps affects permeation more favorably than that of 80 cps for compounds 13 and 14.

TABLE 11

Effect of Wavelength, Photocatalytic Agent and
Pulse Rate on Transdermal Delivery of Enkephalins

| Control or Wavelength | Permeation (µg/cm²/ 24 hrs) of Cmpd. No. 13 at Pulse Rate* 24 cps | Permeation (µg/cm²/ 24 hrs) of Cmpd. No. 13 at Pulse Rate* 80 cps | Permeation (µg/cm²/ 24 hrs) of Cmpd. No. 14 at Pulse Rate* 24 cps | Permeation (µg/cm²/24 hrs) of Cmpd. No. 14 at Pulse Rate* 80 cps |
|---|---|---|---|---|
| Day | 4.44 | 24.44 | 37.31 | 20.89 |
| Day-TiO$_2$ | 8.40 | 18.67 | 46.85 | 18.64 |
| Dark | 34.39 | 21.70 | 107.69 | 18.16 |
| Dark-TiO$_2$ | 1.05 | 20.37 | 67.39 | 20.44 |
| 350 | 94.84 | 30.59 | 84.44 | 31.30 |
| 350 + TiO$_2$ | 103.39 | 32.66 | 73.17 | 28.50 |
| 390 | 68.27 | 38.24 | 108.49 | 31.32 |
| 390 + TiO$_2$ | 103.13 | 35.29 | 103.92 | 31.71 |
| 405 | 108.21 | 26.86 | 87.52 | 20.82 |
| 405 + TiO$_2$ | 206.89 | 13.68 | 284.58 | 13.19 |
| 450 | 298.91 | 27.10 | 29.25 | 21.81 |
| 450 + TiO$_2$ | 153.40 | 28.88 | 173.89 | 29.73 |

*Note that pulse rate does not apply to control samples, e.g. Day, Day-TiO$_2$, Dark and Dark-TiO$_2$.

In addition to testing compounds 13 and 14 in the dark and at defined wavelength ranges, the permeation of these samples was also tested in natural light with no pulse. The objective was to determine the effect that natural light has on the permeation of biologically active substance through the skin surface. The effect of natural light on permeation is more pronounced in compound 14 than in compound 13.

Figure 12A:
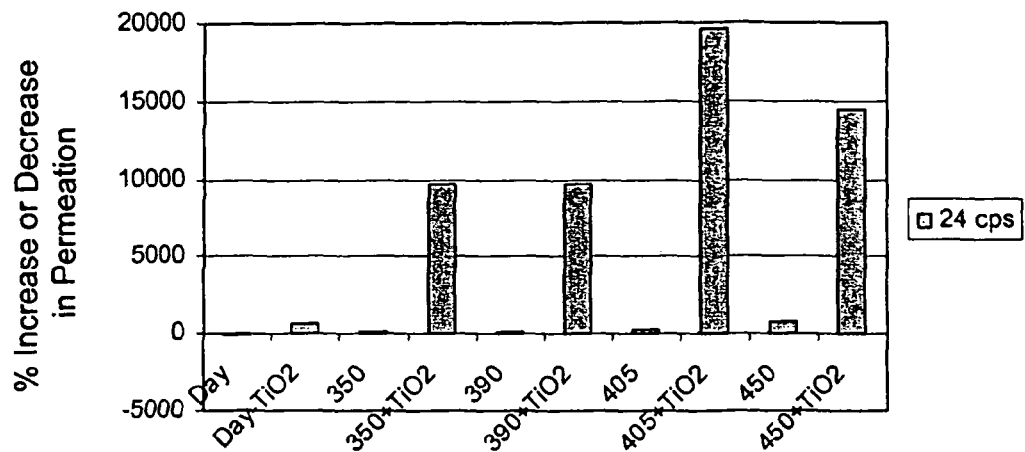
FIG. 12A represents the percent increase or decrease in transdermal permeation of methionine enkephalin acetate as a function of wavelength and photocatalytic agent at a pulse rate of 24 cps. See Example 17.
Figure 12B:
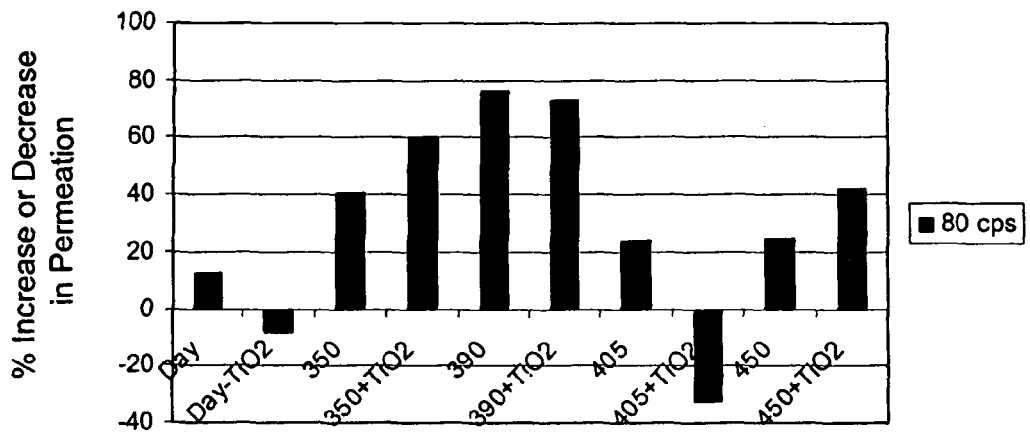
FIG. 12B represents the percent increase or decrease in transdermal permeation of methionine enkephalin acetate as a function of wavelength and photocatalytic agent at a pulse rate of 80 cps. See Example 17.
Figure 12C:
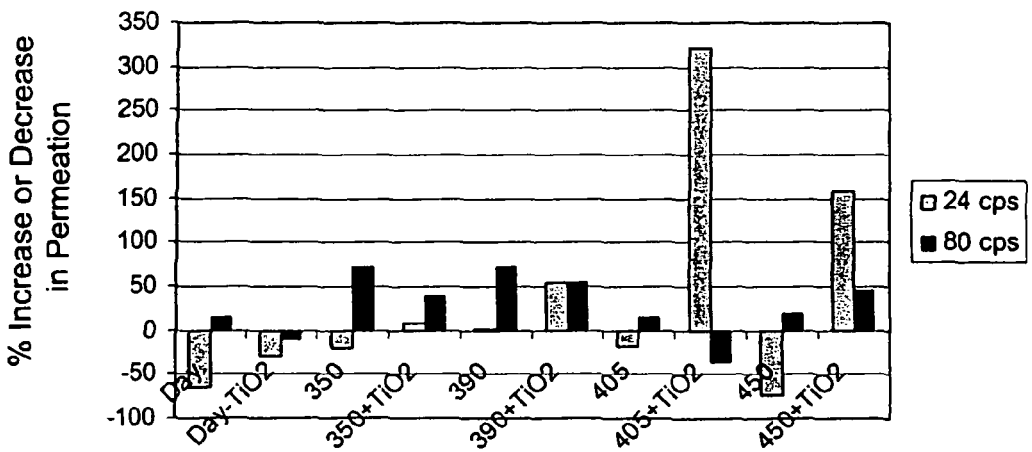
FIG. 12C represents the percent increase or decrease in transdermal permeation of leucine enkephalin as a function of wavelength and photocatalytic agent at pulse rates of 24 and 80 cps. See Example 17.

In order to evaluate data obtained on different skin samples, it was necessary to develop a standardized method for comparing permeation values. To do that, the amounts permeated in the dark were subtracted from the amounts permeated in daylight or at a specified wavelength. The percent increase in permeation was then calculated by equation 1:

$$\% = \frac{(\text{amount permeated} - \text{baseline amount}) * 100}{\text{baseline amount}}, \quad [1]$$

where baseline amount is the amount of permeation under dark or dark-TiO$_2$ controls, depending on whether a photocatalytic agent was present or not. Table 12 lists the % increase or decrease in permeation for compounds 13 and 14 calculated from the values in Table 11 and equation 1. FIGS. 12(A)-(C) correspond to the % permeation increases for compounds 13 and 14 as shown in Table 12.

TABLE 12

Percent Increase or Decrease in Permeation
as a Function of Wavelength, Photocatalytic
Agent and Pulse Rate for Enkephalins

| Control or Wavelength | % Permeation Comp. No. 13 at Pulse Rate* 24 cps | % Permeation Comp. No. 13 at Pulse Rate* 80 cps | % Permeation Comp. No. 14 at Pulse Rate* 24 cps | % Permeation Comp. No. 14 at Pulse Rate* 80 cps |
|---|---|---|---|---|
| Day | −87.09 | 12.63 | −65.35 | 15.03 |
| Day-TiO$_2$ | 700.00 | −8.35 | −30.48 | −8.81 |
| Dark | — | — | — | — |
| Dark-TiO$_2$ | — | — | — | — |
| 350 | 175.78 | 40.97 | −21.59 | 72.36 |
| 350 + TiO$_2$ | 9746.67 | 60.33 | 8.58 | 39.43 |
| 390 | 98.52 | 76.22 | 0.74 | 72.47 |
| 390 + TiO$_2$ | 9721.90 | 73.24 | 54.21 | 55.14 |
| 405 | 214.66 | 23.78 | −18.73 | 14.65 |
| 405 + TiO$_2$ | 19603.81 | −32.84 | 322.29 | −35.47 |
| 450 | 769.18 | 24.88 | −72.84 | 20.10 |
| 450 + TiO$_2$ | 14509.52 | 41.78 | 158.04 | 45.45 |

*Note that pulse rate does not apply to control samples, e.g. Day, Day-TiO$_2$, Dark and Dark-TiO$_2$.

The % increase or decrease in permeation calculated from equation 1 are shown in FIGS. 12(A)-(C). For example, FIG. 12A illustrates that after baseline adjustment, the addition of TiO$_2$ as the photocatalytic agent substantially increases the skin permeation of compound 13 at 24 cps. In contrast, FIG. 12B illustrates that addition of TiO$_2$ to compound 13 does not result in a significant increase or decrease in skin permeation of that compound at 80 cps. According to these data, the most significant increase in permeation occurs around 390 nm in compound 13 (with or without TiO$_2$) at 80 cps whereas the largest increase in permeation for compound 13 around 405 nm (with TiO$_2$) occurred at 24 cps. Similarly, FIG. 12C shows the largest value of permeation for compound 14 occurred at 24 cps and 405 nm (with TiO$_2$). Moreover, compound 14 behaves similarly to compound 13 in that the addition with TiO$_2$ aids in the permeation of compound 14 at 24 cps but does not necessarily aid in this permeation at 80 cps.

Example 18

Figure 13A:
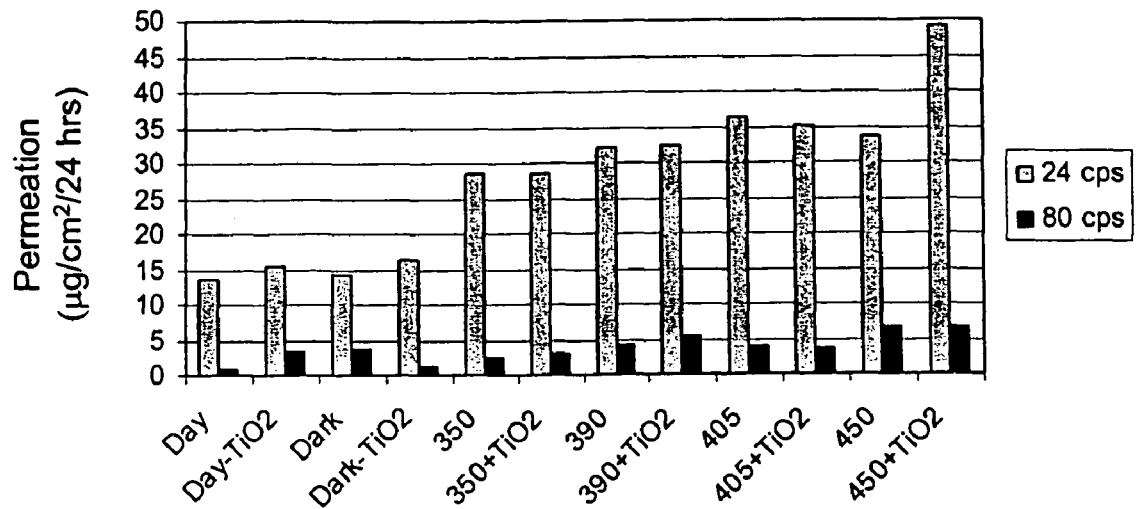
FIG. 13A illustrates the effect of wavelength, photocatalytic agent and pulse rate on transdermal delivery of small peptide, Gly-Tyr. See Example 18.
Figure 13B:
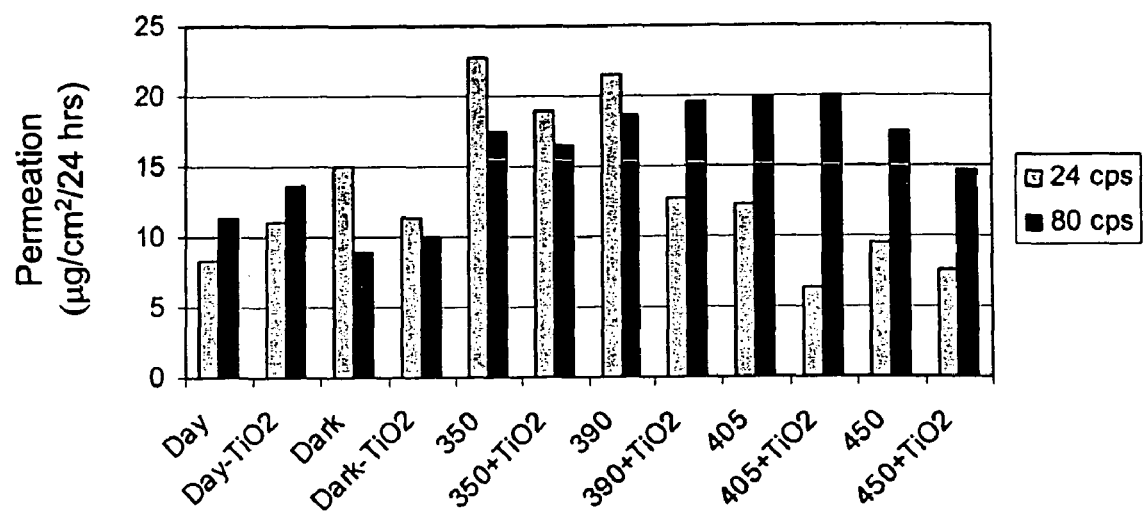
FIG. 13B illustrates the effect of wavelength, photocatalytic agent and pulse rate on transdermal delivery of small peptide, Val-Tyr-Val. See Example 18.

Effect of wavelength, photocatalytic agent and pulse rate on transdermal delivery of small peptides. The permeation of Gly-Tyr (compound 11 from Table 1) and Val-Tyr-Val (compound 12 from Table 1) were tested under various conditions, including wavelength, photocatalytic agent and pulse rate. Table 13 and FIGS. 13A and 13B illustrate permeation of compounds 11 and 12, respectively, under these various conditions. Note that each sample was tested in duplicate and the average value was reported for each condition tested in Table 13. These data demonstrate that a pulse rate of 24 cps affects permeation more favorably than 80 cps for compound 11. FIG. 13B shows that the largest amount of permeation for compound 12 occurred at 350 or 390 nm, both samples lacking TiO$_2$. Although compound 12 has increased permeation at 350 and 390 nm at 24 cps, compound 12 has a larger increase in permeation at wavelengths 405 and 450 nm at 80 cps (see FIG. 13B). Also, at these higher wavelengths, the addition of TiO$_2$ to compound 12 at 24 cps shows a slight reduction in permeation whereas the addition of TiO$_2$ to compound 12 at 80 cps does not show a significant change in permeation.

versus 24 cps. In fact, there is a decrease in permeation for compound 12 at 24 cps in 405 and 450 nm samples.

TABLE 13

Effect of Wavelength, Photocatalytic Agent and Pulse Rate on Transdermal Delivery of Gly-Tyr and Val-Tyr-Val

| Wavelength or Control | Permeation (µg/cm$^2$/24 hrs) Comp. No. 11 Pulse Rate* 24 cps | Permeation (µg/cm$^2$/24 hrs) Comp. No. 11 pulse Rate* 80 cps | Permeation (µg/cm$^2$/24 hrs) Comp. No. 12 Pulse Rate* 24 cps | Permeation (µg/cm$^2$/24 hrs) Comp. No. 12 pulse Rate* 80 cps |
|---|---|---|---|---|
| Day | 13.72 | 0.96 | 8.27 | 11.32 |
| Day-TiO$_2$ | 15.31 | 3.47 | 11.11 | 13.64 |
| Dark | 14.38 | 3.78 | 15.03 | 8.97 |
| Dark-TiO$_2$ | 16.24 | 1.32 | 11.39 | 9.94 |
| 350 | 28.41 | 2.53 | 22.69 | 17.41 |
| 350 + TiO$_2$ | 28.42 | 3.16 | 18.98 | 16.45 |
| 390 | 32.12 | 4.14 | 21.47 | 18.70 |
| 390 + TiO$_2$ | 32.48 | 5.46 | 12.73 | 19.47 |
| 405 | 36.29 | 3.92 | 12.32 | 19.89 |
| 405 + TiO$_2$ | 35.22 | 3.69 | 6.36 | 19.99 |
| 450 | 33.66 | 6.74 | 9.51 | 17.39 |
| 450 + TiO$_2$ | 49.17 | 6.53 | 7.52 | 14.74 |

*Note that pulse rate does not apply to control samples, e.g. Day, Day-TiO$_2$, Dark and Dark-TiO$_2$.

Compounds 11 and 12 were also tested in natural light, without pulse. The effect of natural light on the permeation of compounds 11 and 12 was similar and moreover, the permeation values were on the order of those of the dark controls.

TABLE 14

Percent Increase or Decrease in Permeation as a Function of Wavelength, Photocatalytic Agent and Pulse Rate for Gly-Tyr and Val-Tyr-Val

| Wavelength or Control | % Permeation Comp. No. 11. Pulse Rate* 24 cps | % Permeation Comp. No. 11 Pulse Rate* 80 cps | % Permeation Comp. No. 12 Pulse Rate* 24 cps | % Permeation Comp. No. 12 Pulse Rate* 80 cps |
|---|---|---|---|---|
| Day | −7.80 | −74.60 | −44.98 | 26.20 |
| Day-TiO$_2$ | −5.73 | 162.88 | −2.55 | 37.22 |
| Dark | — | — | — | — |
| Dark-TiO$_2$ | — | — | — | — |
| 350 | 90.93 | −33.07 | 50.96 | 94.09 |
| 350 + TiO$_2$ | 75.00 | 139.39 | 66.64 | 65.49 |
| 390 | 115.86 | 9.52 | 42.85 | 108.47 |
| 390 + TiO$_2$ | 100.00 | 313.64 | 11.76 | 95.88 |
| 405 | 143.88 | 3.70 | −18.03 | 121.74 |
| 405 + TiO$_2$ | 116.87 | 179.55 | −44.16 | 101.11 |
| 450 | 126.34 | 78.31 | −36.73 | 93.87 |
| 450 + TiO$_2$ | 202.77 | 394.70 | −33.98 | 48.29 |

*Note that pulse rate does not apply to control samples, e.g. Day, Day-TiO$_2$, Dark and Dark-TiO$_2$.

Figure 14A:
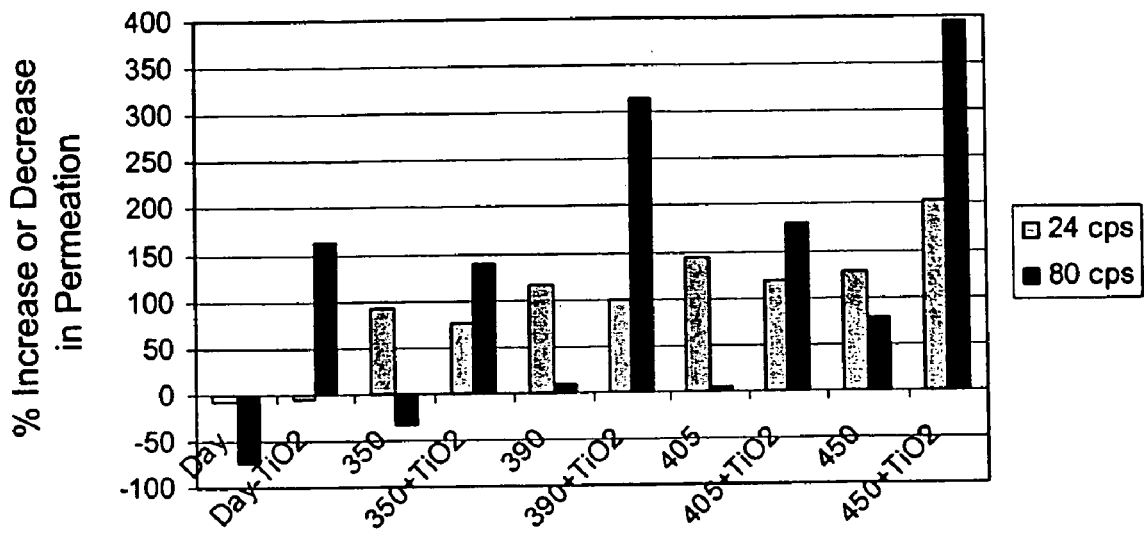
FIG. 14A represents the percent increase or decrease in transdermal permeation of small peptide, Gly-Tyr, as a function of wavelength and photocatalytic agent at pulse rates of 24 and 80 cps. See Example 18.
Figure 14B:
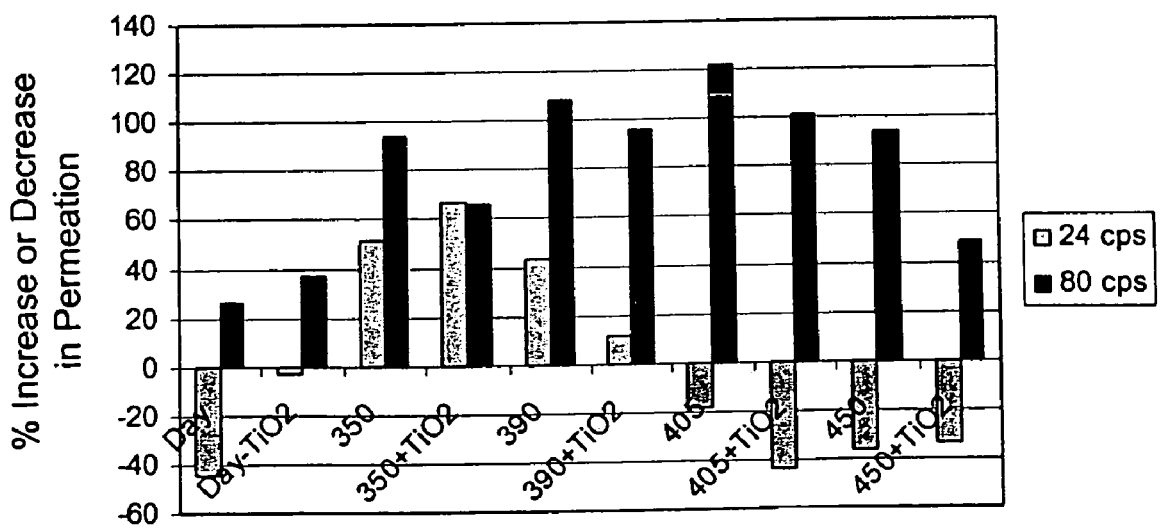
FIG. 14B represents the percent increase or decrease in transdermal permeation of small peptide, Val-Tyr-Val, as a function of wavelength and photocatalytic agent at pulse rates of 24 and 80 cps. See Example 18.

The % increase or decrease in permeation calculated from equation 1 are shown in FIGS. 14A and 14B. For example, FIG. 14A illustrates that after baseline adjustment, the addition of TiO$_2$ as the photocatalytic agent substantially increases the skin permeation of compound 11 at 80 cps. This appears to be in contrast to the data presented in FIG. 13A, where compound 11 appears to be permeated to a greater extent at 24 cps. The differences that occur between these sets of data are due to the differences in the skin samples, i.e., the skin sample variation will be averaged after baseline adjustment to provide a more accurate permeation value. Additionally, FIG. 14B illustrates that for wavelengths 390 nm and above, compound 12 is permeated to a greater extent at 80 cps Example 19

Figure 15A:
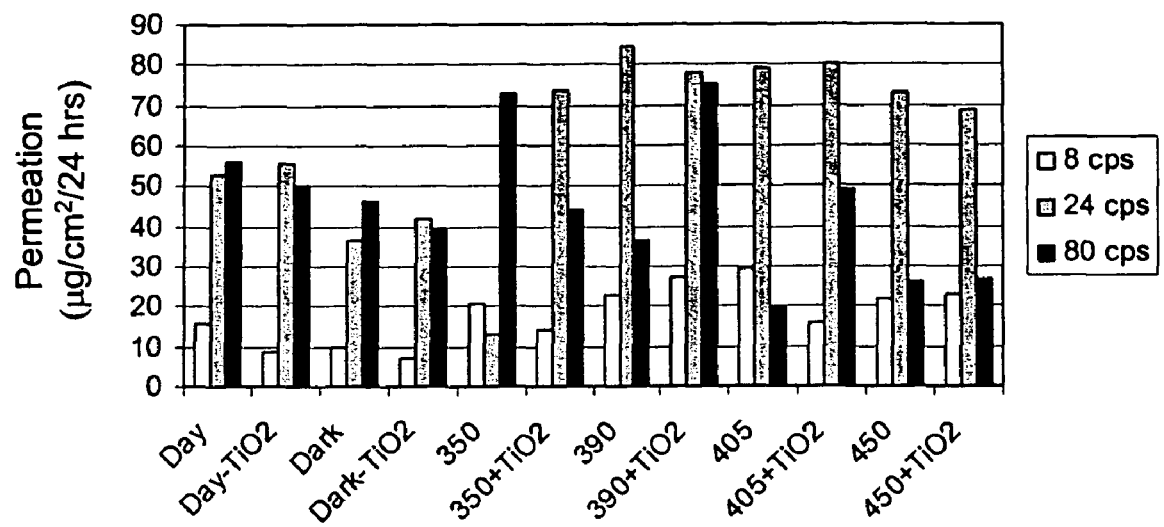
FIG. 15A illustrates the effect of wavelength, photocatalytic agent and pulse rate on transdermal delivery of insulin. See Example 19.
Figure 15B:
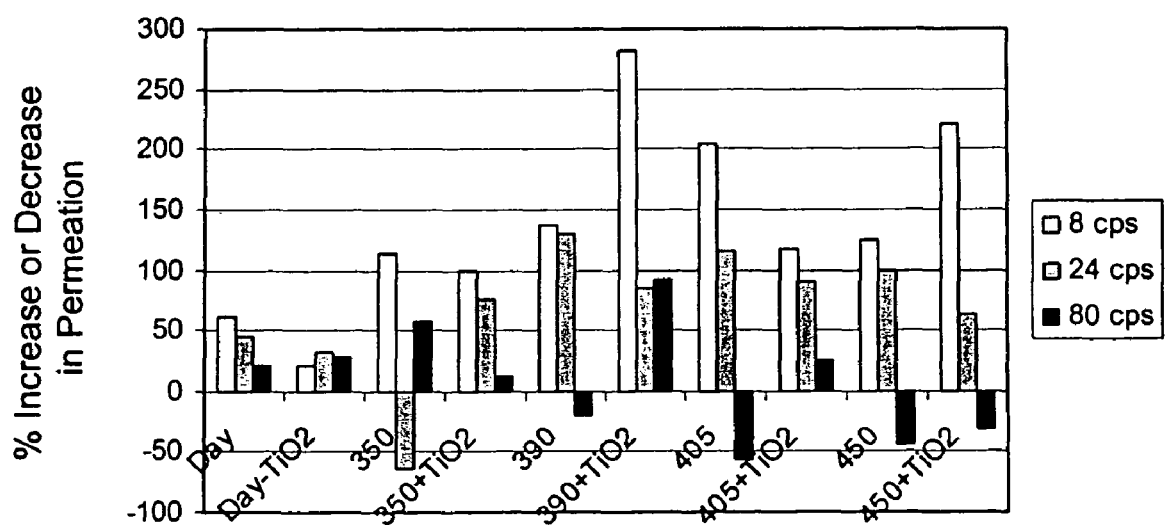
FIG. 15B represents the percent increase or decrease in transdermal permeation of insulin as a function of wavelength and photocatalytic agent at pulse rates of 8, 24 and 80 cps. See Example 19.

Effect of wavelength, photocatalytic agent and pulse rate on transdermal delivery of insulin. The permeation of insulin (compound 19 from Table 1) was also tested under various conditions, including wavelength, photocatalytic agent and pulse rate. Table 15 and FIG. 15A illustrate permeation of compound 19 under these various conditions. Note that each sample was tested in duplicate and the average value was reported for each condition tested in Table 15. These data demonstrate that lower pulse rates result in less permeation but that after standardization using equation 1, the lowest pulse rate of 8 cps caused insulin to absorb to the greatest extent (see Table 16 and FIG. 15B). The effect of natural light on permeation of compound 19 was also tested and shown Tables 15 and 16 and FIGS. 15A and 15B.

TABLE 15

Effect of Wavelength, Photocatalytic Agent and
Pulse Rate on Transdermal Delivery of Insulin

| Wavelength or Control | Permeation ($\mu g/cm^2/24$ hrs) Comp. No. 19 Pulse Rate* 8 cps | Permeation ($\mu g/cm^2/24$ hrs) Comp. No. 19 Pulse Rate* 24 cps | Permeation ($\mu g/cm^2/24$ hrs) Comp. No. 19 Pulse Rate* 80 cps |
|---|---|---|---|
| Day | 15.56 | 52.93 | 56.11 |
| Day-TiO$_2$ | 8.61 | 55.83 | 49.95 |
| Dark | 9.63 | 36.77 | 46.23 |
| Dark-TiO$_2$ | 7.15 | 42.11 | 39.04 |
| 350 | 20.65 | 12.98 | 73.05 |
| 350 + TiO$_2$ | 14.22 | 73.73 | 44.04 |
| 390 | 22.87 | 84.67 | 36.54 |
| 390 + TiO$_2$ | 27.32 | 77.99 | 75.13 |
| 405 | 29.27 | 79.31 | 19.79 |
| 405 + TiO$_2$ | 15.59 | 79.92 | 49.08 |
| 450 | 21.55 | 73.22 | 26.12 |
| 450 + TiO$_2$ | 22.96 | 68.54 | 26.81 |

* Note that pulse rate does not apply to control samples, e.g. Day, Day-TiO$_2$, Dark and Dark-TiO$_2$.

TABLE 16

Percent Increase or Decrease in Permeation
as a Function of Wavelength, Photocatalytic
Agent and Pulse Rate for Insulin

| Wavelength or Control | % Permeation Comp. No. 19 Pulse Rate* 8 cps | % Permeation Comp. No. 19 Pulse Rate* 24 cps | % Permeation Comp. No. 19 Pulse Rate* 80 cps |
|---|---|---|---|
| Day | 61.58 | 43.95 | 21.37 |
| Day-TiO$_2$ | 20.42 | 32.58 | 27.95 |
| Dark | — | — | — |
| Dark-TiO$_2$ | — | — | — |
| 350 | 114.43 | −64.70 | 58.01 |
| 350 + TiO$_2$ | 98.88 | 75.09 | 12.81 |
| 390 | 137.49 | 130.27 | −20.96 |
| 390 + TiO$_2$ | 282.10 | 85.21 | 92.44 |
| 405 | 203.95 | 115.69 | −57.19 |
| 405 + TiO$_2$ | 118.04 | 89.79 | 25.72 |
| 450 | 123.78 | 99.13 | −43.50 |
| 450 + TiO$_2$ | 221.12 | 62.76 | −31.33 |

*Note that pulse rate does not apply to control samples, e.g. Day, Day-TiO$_2$, Dark and Dark-TiO$_2$.

Example 20

Figure 16A:
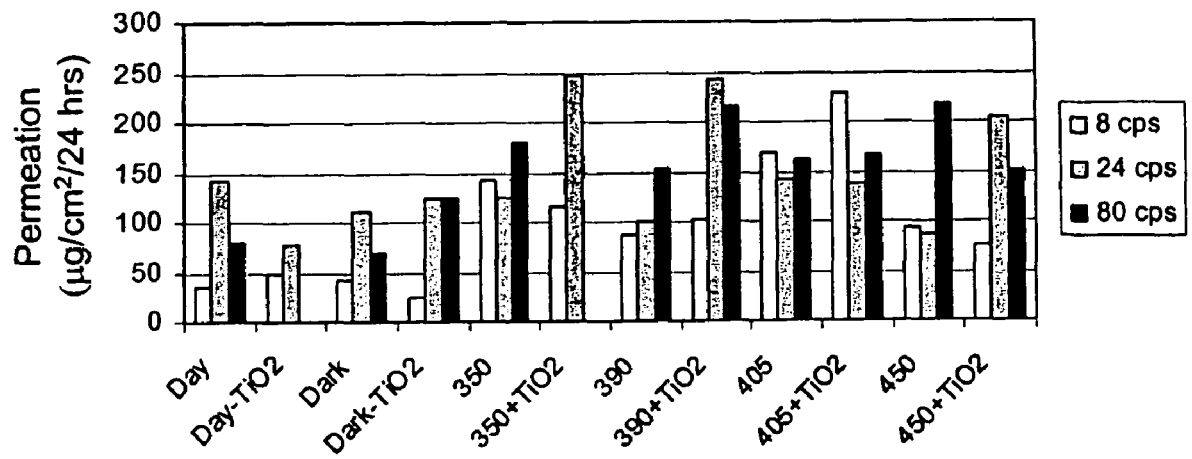
FIG. 16A illustrates the effect of wavelength, photocatalytic agent and pulse rate on transdermal delivery of lidocaine. See Example 20.
Figure 16B:
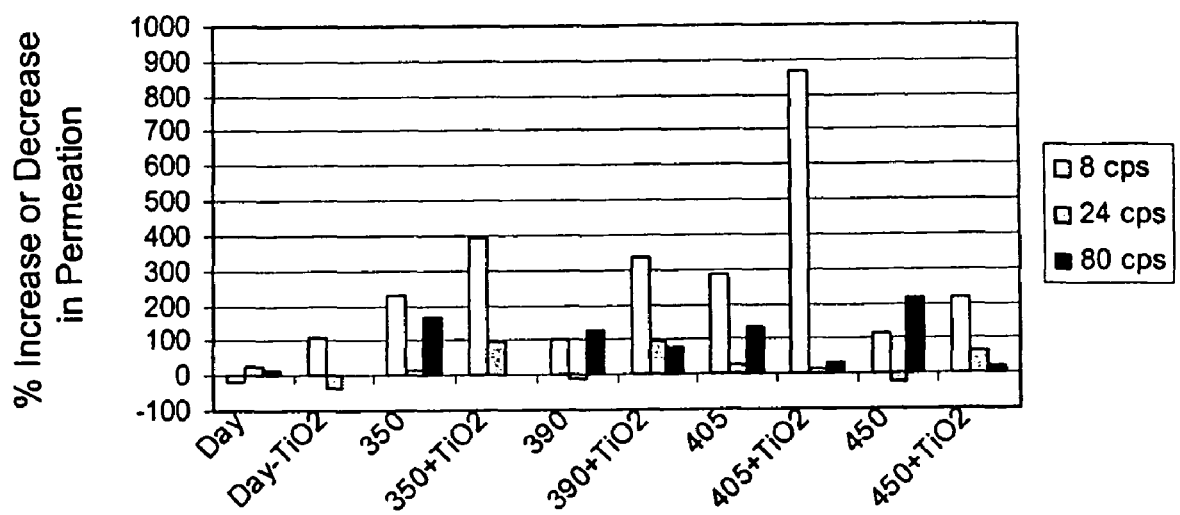
FIG. 16B represents the percent increase or decrease in transdermal permeation of lidocaine as a function of wavelength and photocatalytic agent at pulse rates of 8, 24 and 80 cps. See Example 20.

Effect of wavelength, photocatalytic agent and pulse rate on transdermal delivery of lidocaine. The permeation of lidocaine (compound 20 from Table 1) was also tested under various conditions, including wavelength, photocatalytic agent and pulse rate. Table 17 and FIG. 16A illustrate permeation of compound 20 under these various conditions. Note that each sample was tested in duplicate and the average value was reported for each condition tested (see Table 17). These data demonstrate that a pulse rate of 24 cps and the addition of TiO$_2$ aids in the permeation of compound 20 through a skin surface. Again, after baseline adjustment using equation 1 (see Table 18 and FIG. 16B), the data look slightly different in that a pulse rate of 8 cps and the addition of TiO$_2$ appears to enhance the permeation of compound 20 in the skin.

TABLE 17

Effect of Wavelength, Photocatalytic Agent and
Pulse Rate on Transdermal Delivery of Lidocaine

| Wavelength or Control | Permeation ($\mu g/cm^2/24$ hrs) Comp. No. 20 Pulse Rate* 8 cps | Permeation ($\mu g/cm^2/24$ hrs) Comp. No. 20 Pulse Rate* 24 cps | Permeation ($\mu g/cm^2/24$ hrs) Comp. No. 20 Pulse Rate* 80 cps |
|---|---|---|---|
| Day | 35.99 | 141.16 | 80.05 |
| Day-TiO$_2$ | 49.34 | 78.78 | — |
| Dark | 43.29 | 110.88 | 68.67 |
| Dark-TiO$_2$ | 23.60 | 123.71 | 124.21 |
| 350 | 141.60 | 125.32 | 180.48 |
| 350 + TiO$_2$ | 116.33 | 245.86 | — |
| 390 | 87.06 | 100.80 | 154.33 |
| 390 + TiO$_2$ | 102.51 | 241.46 | 216.19 |
| 405 | 167.87 | 143.20 | 161.80 |
| 405 + TiO$_2$ | 227.82 | 137.18 | 167.05 |
| 450 | 94.37 | 86.24 | 218.60 |
| 450 + TiO$_2$ | 74.79 | 204.28 | 150.31 |

*Note that pulse rate does not apply to control samples, e.g. Day, Day-TiO$_2$, Dark and Dark-TiO$_2$.

TABLE 18

Percent Increase or Decrease in Permeation as a
Function of Wavelength, Photocatalytic Agent and Pulse Rate
for Lidocaine

| Wavelength or Control | % Permeation Comp. No. 20 Pulse Rate* 8 cps | % Permeation Comp. No. 20 Pulse Rate* 24 cps | % Permeation Comp. No. 20 Pulse Rate* 80 cps |
|---|---|---|---|
| Day | −16.86 | 27.31 | 16.57 |
| Day-TiO$_2$ | 109.07 | −36.32 | — |
| Dark | — | — | — |
| Dark-TiO$_2$ | — | — | — |
| 350 | 227.10 | 13.02 | 162.82 |
| 350 + TiO$_2$ | 392.92 | 98.74 | — |
| 390 | 101.11 | −9.09 | 124.74 |
| 390 + TiO$_2$ | 334.36 | 95.18 | 74.05 |
| 405 | 287.78 | 29.15 | 135.62 |
| 405 + TiO$_2$ | 865.34 | 10.89 | 34.49 |
| 450 | 117.99 | −22.22 | 218.33 |
| 450 + TiO$_2$ | 216.91 | 65.13 | 21.01 |

*Note that pulse rate does not apply to control samples, e.g. Day, Day-TiO$_2$, Dark and Dark-TiO$_2$.

Figure 17:
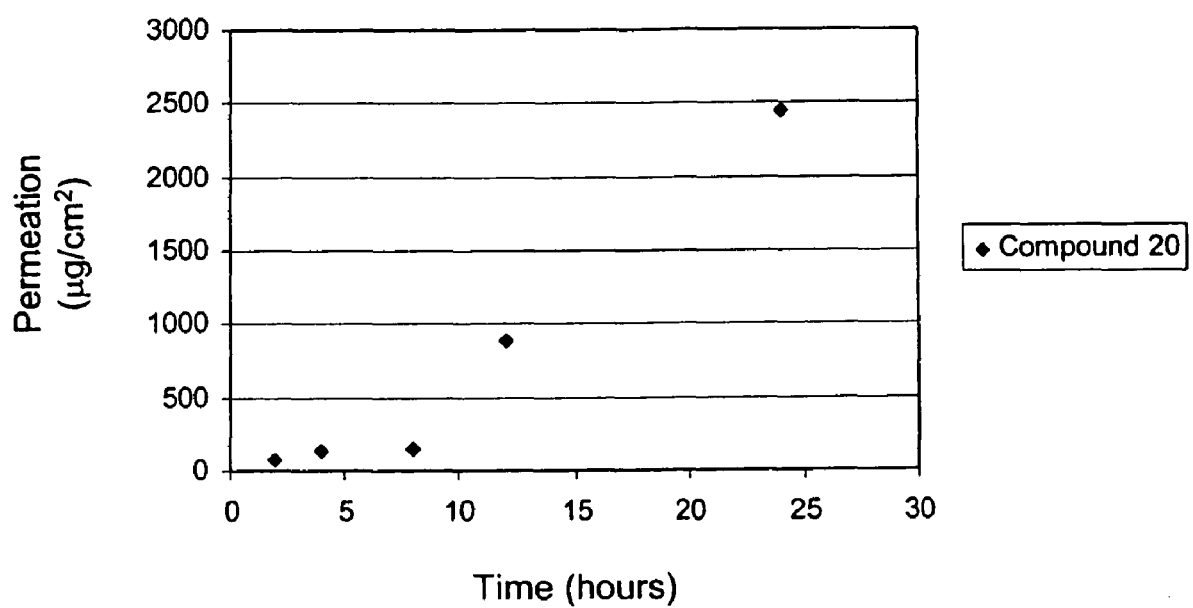
FIG. 17 shows permeation of lidocaine as a function of time. See Example 20.
Figure 18A:
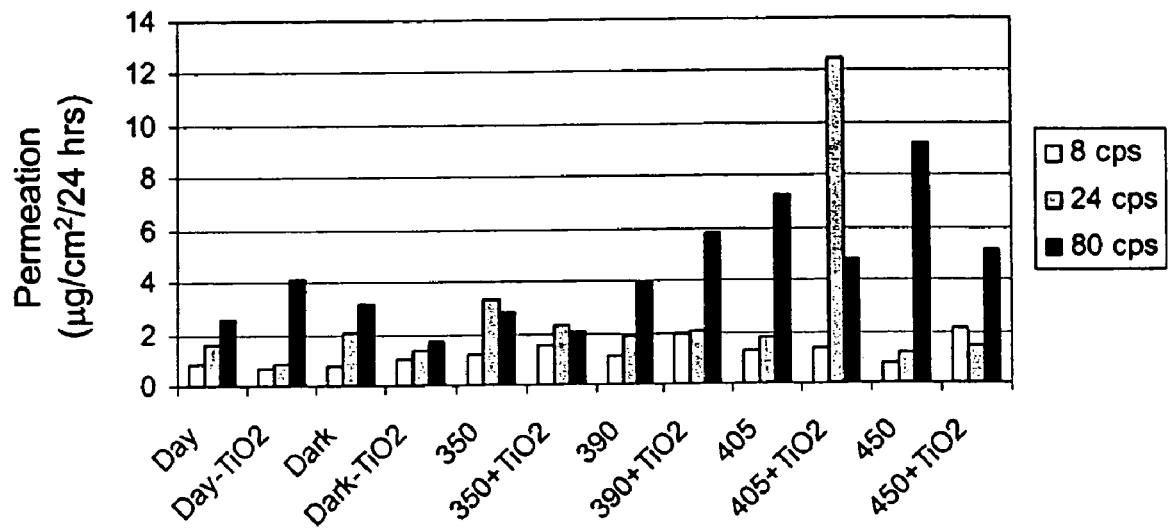
FIG. 18A illustrates the effect of wavelength, photocatalytic agent and pulse rate on transdermal delivery of amphotericin B. See Example 21.
Figure 18B:
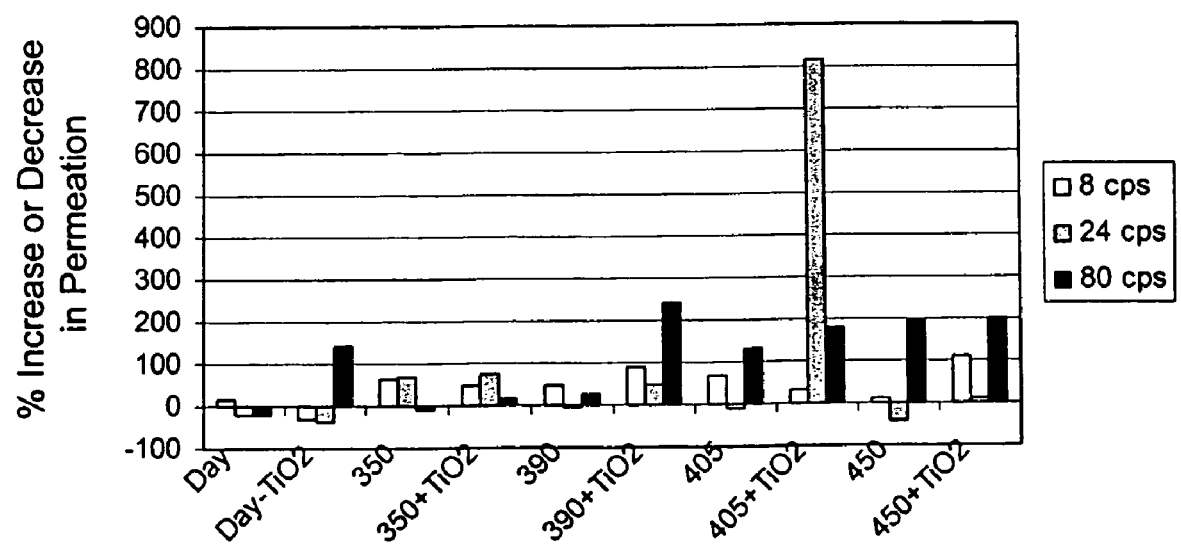
FIG. 18B represents the percent increase or decrease in transdermal permeation of amphotericin B as a function of wavelength and photocatalytic agent at pulse rates of 8, 24 and 80 cps. See Example 21.

In addition to the permeation data above, a kinetic study were also performed on compound 20. For example, permeation ($\mu g/cm^2$) was monitored as a function of time (see Table 19 and FIG. 17). For this test, side-by-side Franz cells were used and a 405 nm LED was immersed in the donor cell solution. Aliquots of 250 $\mu$L were removed from the receiving cell while 250 $\mu$L of HPLC grade water was simultaneously added back to the donor cell. The data show a lag time and steep slope, with the 24 hour point possibly representing a change in curve. In addition, the immersion of the LED in the donor solution caused more of compound 20 to permeate the skin than when the compound was merely pulsed with an LED not in contact with the solution.

TABLE 19

Permeation as a Function of Time for Lidocaine

| Time (hours) | Permeation ($\mu g/cm^2$) |
|---|---|
| 2 | 73.28 |
| 4 | 130.02 |

TABLE 19-continued

Permeation as a Function of Time for Lidocaine

| Time (hours) | Permeation ($\mu g/cm^2$) |
|---|---|
| 8 | 157.08 |
| 12 | 890.89 |
| 24 | 2446.69 |

Example 21

Effect of wavelength, photocatalytic agent and pulse rate on transdermal delivery of Amphotericin B. The permeation of amphotericin B (compound 21 from Table 1) was also tested under various conditions, including wav

```
<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Tyr Gly Gly Phe Leu
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Asp Arg Val Tyr Ile His Pro Phe
1               5
```

We claim:

1. A composition for photokinetic delivery of a biologically active substance using pulsed incoherent light, comprising a biologically active substance, a solvent, a gelling agent and a photocatalytic agent, wherein said photocatalytic agent has a band gap energy of between about 2.9 eV and about 3.2 eV.

2. The composition according to claim 1, wherein said photocatalytic agent is present in said composition at a concentration of between 0.001% and 20% (w/w).

3. The composition according to claim 1, wherein said photocatalytic agent is present in said composition at a concentration of 2% (w/w).

4. The composition according to claim 1, wherein said biologically active substance is present in said composition at a concentration of between 0.01% and 2% (w/v).

5. The composition according to claim 1, wherein said biologically active substance is present in said composition at a concentration of between 0.05% and 1% (w/v).

6. The composition according to claim 1, wherein said gelling agent is present in said composition at a concentration of between 0.1% and 10% (w/v).

7. The composition according to claim 1, wherein said gelling agent is present in said composition at a concentration of 1% (w/v).

8. The composition according to claim 1, wherein the biologically active substance is a polar compound selected from the group consisting of theophylline-7 acetic acid, sodium ascorbyl phosphate, ascorbic acid, ascorbyl palmitate, pyridoxine, and nicotinic acid.

9. The composition according to claim 1, wherein the biologically active substance is a non-polar compound selected from the group consisting of theobromine, theophylline, caffeine, and nicotinamide.

10. The composition according to claim 1, wherein the biologically active substance is selected from the group consisting of an analgesic, an anaesthetic, an antacid, an antianxiety drug, an antiarrhythmic, an antibacterial, an antibiotic, an anticoagulant and thrombolytic, an anticonvulsant, an antidepressant, an antidiarrheal, an antiemetic, an antifungal, an antihistamine, an antihypertensive, an anti-inflammatory, an antieoplastic, an antipsychotic, an antipyretic, an antiviral, a barbiturate, a beta-blocker, a bronchodilator, a cold cure, a corticosteroid, a cough suppressant, a cytotoxic, a decongestant, a diuretic, an expectorant, a hypoglycemic, an immunosuppressive, a laxative, a muscle relaxant, a sedative, a sex hormone, a sleeping drug, a tranquilizer, and a vitamin.

11. The composition according to claim 1, wherein the biologically active substance is selected from the group consisting of an analgesic, an anaesthetic, an antacid, an antianxiety drug, an antiarrhythmic, an antibacterial, an antibiotic, an anticoagulant and thrombolytic, an anticonvulsant, an antidiarrheal, an antiviral, a barbiturate, a cytotoxics, and a vitamin.

12. The composition according to claim 1, wherein the biologically active substance is an anaesthetic.

13. The composition according to claim 12, wherein the anaesthetic is lidocaine.

14. The composition according to claim 1, wherein said biologically active substance is a peptide.

15. The composition according to claim 14, wherein the peptide is selected from the group consisting of Gly-Tyr, Val-Tyr-Val, Tyr-Gly-Gly-Phe-Met (SEQ ID NO: 1), Tyr-Gly-Gly-Phe-Leu (SEQ ID NO: 2), and Asp-Arg-Val-Tyr-Ile-His-Pro-Phe (SEQ ID NO: 3).

16. The composition according to claim 1, wherein said biologically active substance is a hormone.

17. The composition according to claim 16, wherein the hormone is selected from the group consisting of methionine enkephalin acetate, leucine enkephalin, angiotensin II acetate, β-estradiol, methyl testosterone, progesterone and insulin.

18. The composition according to claim 1, wherein said biologically active substance is a protein.

19. The composition according to claim 18, wherein the protein is selected from the group consisting of an enzyme, an antibody, and a glycoprotein.

20. The composition according to claim 1, wherein said biologically active substance is an antibiotic.

21. The composition according to claim 20, wherein the antibiotic is amphotericin B.

22. The composition according to claim 1, wherein said gelling agent is selected from the group consisting of hydroxypropyl cellulose, hydroxyethyl cellulose, agar, pectine, alginic acid and its salts, guar gum, polyvinyl alcohol, polyethylene oxide, cellulose and its derivatives, propylene carbonate, polyethylene glycol, hexylene glycol sodium carboxymethylcellulose, polyacrylates, polyoxyethylene-polyoxypropylene block copolymers, pluronics, wood wax alcohols and tyloxapol.

23. The composition according to claim 22, wherein said gelling agent is hydroxypropyl cellulose.

24. The composition according to claim 1, wherein said photocatalytic agent is selected from the group consisting of a rutile form of titanium dioxide, an anatase form of titanium dioxide, a brookite form of titanium dioxide, ZnO, $ZrO_2$ and $Sc_2O_3$.

25. The composition according to claim 24, wherein said photocatalytic agent is a rutile form of titanium dioxide.

26. The composition according to claim 1, wherein said solvent is an aqueous or an organic solvent.

27. The composition according to claim 26, wherein the solvent is water.

28. The composition according to claim 26, wherein the solvent is an aqueous solution of ethyl lactate or propylene glycol or both.

* * * * *